(12) United States Patent
Kawahara et al.

(10) Patent No.: US 9,029,519 B2
(45) Date of Patent: May 12, 2015

(54) MODIFIED PROMOTER

(75) Inventors: Akihito Kawahara, Haga-gun (JP);
Hiroshi Kodama, Haga-gun (JP);
Katsutoshi Ara, Haga-gun (JP)

(73) Assignee: Kao Corporation, Tokyo (JP)

(*) Notice: Subject to any disclaimer, the term of this patent is extended or adjusted under 35 U.S.C. 154(b) by 586 days.

(21) Appl. No.: 13/499,480

(22) PCT Filed: Oct. 18, 2010

(86) PCT No.: PCT/JP2010/068783
§ 371 (c)(1),
(2), (4) Date: Mar. 30, 2012

(87) PCT Pub. No.: WO2011/049227
PCT Pub. Date: Apr. 28, 2011

(65) Prior Publication Data
US 2012/0183998 A1   Jul. 19, 2012

(30) Foreign Application Priority Data

Oct. 21, 2009   (JP) ................................. 2009-242178
Oct. 1, 2010    (JP) ................................. 2010-224065

(51) Int. Cl.
| | | |
|---|---|---|
| *C07H 21/04* | (2006.01) | |
| *C12N 15/75* | (2006.01) | |
| *C12N 15/66* | (2006.01) | |
| *C12P 21/02* | (2006.01) | |
| *C12N 15/11* | (2006.01) | |
| *C12N 1/20* | (2006.01) | |

(52) U.S. Cl.
CPC ................ *C12N 15/75* (2013.01); *C12N 15/66* (2013.01); *C12P 21/02* (2013.01); *C12N 15/11* (2013.01); *C12N 1/20* (2013.01)

(58) Field of Classification Search
None
See application file for complete search history.

(56) References Cited

U.S. PATENT DOCUMENTS

| 6,743,616 B2* | 6/2004 | Araki et al. ................... 435/202 |
|---|---|---|
| 2002/0123124 A1 | 9/2002 | Araki et al. |
| 2008/0014608 A1 | 1/2008 | Endo et al. |
| 2011/0021751 A1 | 1/2011 | Takimura et al. |

FOREIGN PATENT DOCUMENTS

| CN | 1930291 A | 3/2007 |
|---|---|---|
| JP | 2000-078981 A | 3/2000 |
| JP | 2000-210081 A | 8/2000 |
| JP | 2002-112792 A | 4/2002 |
| WO | WO 2009/119876 A1 | 10/2009 |

OTHER PUBLICATIONS

"Notification of First Office Action" for Chinese patent application No. 201080046567.2, mailed Dec. 24, 2012, from the Patent Office of the People's Republic of China, Beijing, China.
Miwa, T et al.,"Evaluation and characterization of catabolite-responsive elements (cre) of *Bacillus subtilis*," Nucleic Acids Res., Mar. 2000, 28:1206-1210, Oxford University Press, London, England.
Shaw, G.-C. et al., "Cloning, expression, and catabolite repression of a gene encoding β-galactosidase of *Bacillus megaterium* ATCC 14581," J. Bact., Sep. 1998, 180:4734-4738, Am. Soc. Microbiology, Washington, DC.
International Search Report (ISR) for PCT/JP2010/0068783, I.A. fd: Oct. 18, 2010, mailed Mar. 2, 2011 from the European Patent Office, Rijswijk, Netherlands.
Written Opinion of the International Searching Authority (PCT Rule 43bis.1) for PCT/JP2010-068783, I.A. fd: Oct. 18, 2010, issued Apr. 21, 2012, from the European Patent Office, Munich, Germany.
Sumitomo, N et al., "Application of the upstream region of a *Bacillus* endoglucanase gene to high-level expression of foreign genes in *Bacillus subtilis*," Biosci Biotechnol Biochem 59(11): 2172-2175 (Nov. 1995), Japan Society for Bioscience, Biotechnology, and Agrochemistry, Tokyo, Japan.
Hakamada, Y et al., "Deduced amino acid sequence and possible catalytic residues of a thermostable, alkaline cellulase from an *Alkaliphilic bacillus* strain," Biosci Biotechnol Biochem 64(11): 2281-2289 (Nov. 2000), Japan Society for Bioscience, Biotechnology, and Agrochemistry, Tokyo, Japan.
Weickert MJ et al., "Site-directed mutagenesis of a catabolite repression operator sequence in *Bacillus subtilis*," Proc Natl Acad Sci USA 87: 6238-6242 (Aug. 1990), National Academy of Sciences, Washington, DC.
Inácio JM et al., "Distinct molecular mechanisms involved in carbon catabolite repression of the arabinose regulon in *Bacillus subtilis*," Microbiology 149: 2345-2355 (Sep. 2003), Society for General Microbiology, Reading, U.K.
Martin-Verstraete, I et al., "Two different mechanisms mediate catabolite repression of the *Bacillus subtilis* levanase operon," J. Bacteriol. 177: 6919-6927 (Dec. 1995), Am. Soc. for Microbiology, Washington, DC.
Sumitomo, N. et al., "Nucleotide sequence of the gene for an alkaline endoglucanase from an alkalophilic *Bacillus* and its expression in *Escherichia coli* and *Bacillus subtilis*," Biosci Biotechnol Biochem 56(6): 872-877 (Jun. 1992), Japan Society for Bioscience, Biotechnology, and Agrochemistry, Tokyo, Japan.

(Continued)

*Primary Examiner* — Jim Ketter
(74) *Attorney, Agent, or Firm* — Sterne, Kessler, Goldstein & Fox P.L.L.C.

(57) ABSTRACT

The present invention provides a modified promoter, an expression vector and a transformant each containing the promoter, and a method for producing a gene product of interest using the transformant. The invention provides a modified promoter, including a nucleotide sequence of a promoter derived from bacterium belonging to the genus *Bacillus* in which at least one nucleotide sequence selected from the following has been modified: a nucleotide sequence represented by SEQ ID NO: 1; a nucleotide sequence equivalent to the nucleotide sequence represented by SEQ ID NO: 1, except that one or a plurality of bases therein are substituted, deleted, added or inserted; and a nucleotide sequence having a sequence identity of 70% or more with respect to the nucleotide sequence represented by SEQ ID NO: 1.

10 Claims, 3 Drawing Sheets

(56) References Cited

OTHER PUBLICATIONS

Miwa Y et al., "Involvement of Two Distinct Catabolite-Responsive Elements in Catabolite Repression of the *Bacillus subtilis myo*-Inositol (*iol*) Operon," J. Bacteriol., Oct. 2001; 183: 5877-5884, American Society for Microbiology, Washington, DC.

Kim, Si et al., "Improvement of the production of foreign proteins using a heterologous secretion vector system in *Bacillus subtilis*: effects of resistance to glucose-mediated catabolite repression," Mol Cells, Dec. 1997; 7(6): 788-794, Korean Society for Molecular and Cellular Biology, Seoul, South Korea.

Kant, S et al., "Identification of a Catabolite-Responsive Element Necessary for Regulation of the *cry4A* Gene of *Bacillus thuringiensis* subsp. *israelensis*," J. Bacteriol., Jul. 2009; 191: 4687-4692, American Society for Microbiology, Washington, DC, published ahead of print on May 22, 2009.

Sumitomo, N et al., "Application of the upstream region of a *Bacillus* endoglucanase gene to high-level expression of foreign genes in *Bacillus subtilis*," Biosci Biotechnol Biochem, Nov. 1995; 59(11): 2172-2175, Japan Society for Bioscience, Biotechnology, and Agrochemistry, Taylor & Francis, Abingdon, UK.

Sumitomo, N. et al., "Nucleotide sequence of the gene for an alkaline endoglucanase from an alkalophilic *Bacillus* and its expression in *Escherichia coli* and *Bacillus subtilis*," Biosci Biotechnol Biochem, Jun. 1992; 56(6): 872-877, Japan Society for Bioscience, Biotechnology, and Agrochemistry, Taylor & Francis, Abingdon, UK.

\* cited by examiner

SEQUENCE LISTING

```
<160> NUMBER OF SEQ ID NOS: 14

<210> SEQ ID NO 1
<211> LENGTH: 13
<212> TYPE: DNA
<213> ORGANISM: Bacillus sp.

<400> SEQUENCE: 1
tgtaagcggt taa                                                     13

<210> SEQ ID NO 2
<211> LENGTH: 13
<212> TYPE: DNA
<213> ORGANISM: Bacillus sp.

<400> SEQUENCE: 2
cgaaagcggt tta                                                     13

<210> SEQ ID NO 3
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)

<400> SEQUENCE: 3
agtacttacc attttagagt caaaagatag aagccaagca ggatttgccg atgcaaccgg      60
cttatattta gagggaattt cttttttaaat tgaatacgga ataaaatcag gtaaacaggt    120
cctgatttta ttttttttgaa ttttttttgag aactaaagat tgaaatagaa gtagaagaca   180
acggacataa gaaaattgta ttagttttaa ttatagaaaa cgcttttcta taattattta    240
tacctagaac gaaaatactg tttcgaaagc ggttactat aaaaccttat attccggctc     300
ttttttttaa caggggggtga aaattcactc tagtattcta atttcaacat gctataataa   360
atttgtaaga cgcaatatac atctttttttt tatgatattt gtaagcggtt aaccttgtgc   420
tatatgccga tttaggaagg gggtagattg agtcaagtag tcataattta gataacttat    480
aagttgttga gaagcaggag agaatctggg ttactcacaa gttttttaaa acattatcga    540
```

```
                                              -continued aagcactttc ggttatgctt atgaatttag ctatttgatt caattacttt aataatttta      600 ggaggtaat atg atg tta aga aag aaa aca aag cag ttg att tct tcc att      651
          Met Met Leu Arg Lys Lys Thr Lys Gln Leu Ile Ser Ser Ile
              -25                     -20 ctt att tta gtt tta ctt cta tct tta ttt ccg aca gct ctt gca gca        699
Leu Ile Leu Val Leu Leu Leu Ser Leu Phe Pro Thr Ala Leu Ala Ala
-15                 -10                 -5                  -1  1 gaa gga aac act cgt gaa gac aat ttt aaa cat tta tta ggt aat gac        747
Glu Gly Asn Thr Arg Glu Asp Asn Phe Lys His Leu Leu Gly Asn Asp
                5                   10                  15 aat gtt aaa cgc cct tct gag gct ggc gca tta caa tta caa gaa gtc        795
Asn Val Lys Arg Pro Ser Glu Ala Gly Ala Leu Gln Leu Gln Glu Val
        20                  25                  30 gat gga caa atg aca tta gta gat caa cat gga gaa aaa att caa tta        843
Asp Gly Gln Met Thr Leu Val Asp Gln His Gly Glu Lys Ile Gln Leu
            35                  40                  45 cgt gga atg agt aca cac gga tta caa tgg ttt cct gag atc ttg aat        891
Arg Gly Met Ser Thr His Gly Leu Gln Trp Phe Pro Glu Ile Leu Asn
50                  55                  60                  65 gat aac gca tac aaa gct ctt gct aac gat tgg gaa tca aat atg att        939
Asp Asn Ala Tyr Lys Ala Leu Ala Asn Asp Trp Glu Ser Asn Met Ile
                70                  75                  80 cgt cta gct atg tat gtc ggt gaa aat ggc tat gct tca aat cca gag        987
Arg Leu Ala Met Tyr Val Gly Glu Asn Gly Tyr Ala Ser Asn Pro Glu
            85                  90                  95 tta att aaa agc aga gtc att aaa gga ata gat ctt gct att gaa aat       1035
Leu Ile Lys Ser Arg Val Ile Lys Gly Ile Asp Leu Ala Ile Glu Asn
        100                 105                 110 gac atg tat gtc atc gtt gat tgg cat gta cat gca cct ggt gat cct       1083
Asp Met Tyr Val Ile Val Asp Trp His Val His Ala Pro Gly Asp Pro
115                 120                 125 aga gat ccc gtt tac gct gga gca gaa gat ttc ttt aga gat att gca       1131
Arg Asp Pro Val Tyr Ala Gly Ala Glu Asp Phe Phe Arg Asp Ile Ala
                135                 140                 145
130 gca tta tat cct aac aat cca cac att att tat gag tta gcg aat gag       1179
Ala Leu Tyr Pro Asn Asn Pro His Ile Ile Tyr Glu Leu Ala Asn Glu
            150                 155                 160 cca agt agt aac aat aat ggt gga gct ggg att cca aat aat gaa gaa       1227
Pro Ser Ser Asn Asn Asn Gly Gly Ala Gly Ile Pro Asn Asn Glu Glu
        165                 170                 175 ggt tgg aat gcg gta aaa gaa tac gct gat cca att gta gaa atg tta       1275
Gly Trp Asn Ala Val Lys Glu Tyr Ala Asp Pro Ile Val Glu Met Leu
            180                 185                 190 cgt gat agc ggg aac gca gat gac aat att atc att gtg ggt agt cca       1323
Arg Asp Ser Gly Asn Ala Asp Asp Asn Ile Ile Ile Val Gly Ser Pro
195                 200                 205 aac tgg agt cag cgt cct gac tta gca gct gat aat cca att gat gat       1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct       1419
His His Thr Met Tyr Thr Val His Phe Tyr Thr Gly Ser His Ala Ala
                230                 235                 240 tca act gaa agc tat ccg cct gaa act cct aac tct gaa aga gga aac       1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt       1515
Val Met Ser Asn Thr Arg Tyr Ala Leu Glu Asn Gly Val Ala Val Phe
        260                 265                 270
```

```
                                                        -continued gca aca gag tgg gga act agc caa gca aat gga gat ggt ggt cct tac      1563
Ala Thr Glu Trp Gly Thr Ser Gln Ala Asn Gly Asp Gly Gly Pro Tyr
    275                 280                 285 ttt gat gaa gca gat gta tgg att gag ttt tta aat gaa aac aac att      1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca      1659
Ser Trp Ala Asn Trp Ser Leu Thr Asn Lys Asn Glu Val Ser Gly Ala
                310                 315                 320 ttt aca cca ttc gag tta ggt aag tct aac gca aca agt ctt gac cca      1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa      1755
Gly Pro Asp Gln Val Trp Val Pro Glu Glu Leu Ser Leu Ser Gly Glu
        340                 345                 350 tat gta cgt gct cgt att aaa ggt gtg aac tat gag cca atc gac cgt      1803
Tyr Val Arg Ala Arg Ile Lys Gly Val Asn Tyr Glu Pro Ile Asp Arg
    355                 360                 365 aca aaa tac acg aaa gta ctt tgg gac ttt aat gat gga acg aag caa      1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag      1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat      1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt      1995
Val Ser Glu Gly Asn Tyr Trp Ala Asn Ala Arg Leu Ser Ala Asp Gly
        420                 425                 430 tgg gga aaa agt gtt gat att tta ggt gct gaa aaa ctt act atg gat      2043
Trp Gly Lys Ser Val Asp Ile Leu Gly Ala Glu Lys Leu Thr Met Asp
    435                 440                 445 gtg att gtt gat gag ccg acc acg gta tca att gct gca att cca caa      2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag      2139
Gly Pro Ser Ala Asn Trp Val Asn Pro Asn Arg Ala Ile Lys Val Glu
                470                 475                 480 cca act aat ttc gta ccg tta gga gat aag ttt aaa gcg gaa tta act      2187
Pro Thr Asn Phe Val Pro Leu Gly Asp Lys Phe Lys Ala Glu Leu Thr
            485                 490                 495 ata act tca gct gac tct cca tcg tta gaa gct att gcg atg cat gct      2235
Ile Thr Ser Ala Asp Ser Pro Ser Leu Glu Ala Ile Ala Met His Ala
        500                 505                 510 gaa aat aac aac atc aac aac atc att ctt ttt gta gga act gaa ggt      2283
Glu Asn Asn Asn Ile Asn Asn Ile Ile Leu Phe Val Gly Thr Glu Gly
    515                 520                 525 gct gat gtt atc tat tta gat aac att aaa gta att gga aca gaa gtt      2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct      2379
Glu Ile Pro Val Val His Asp Pro Lys Gly Glu Ala Val Leu Pro Ser
                550                 555                 560 gtt ttt gaa gac ggt aca cgt caa ggt tgg gac tgg gct gga gag tct      2427
Val Phe Glu Asp Gly Thr Arg Gln Gly Trp Asp Trp Ala Gly Glu Ser
            565                 570                 575 ggt gtg aaa aca gct tta aca att gaa gaa gca aac ggt tct aac gcg      2475
Gly Val Lys Thr Ala Leu Thr Ile Glu Glu Ala Asn Gly Ser Asn Ala
        580                 585                 590
```

```
tta tca tgg gaa ttt gga tac cca gaa gta aaa cct agt gat aac tgg     2523
Leu Ser Trp Glu Phe Gly Tyr Pro Glu Val Lys Pro Ser Asp Asn Trp
    595                 600                 605 gca aca gct cca cgt tta gat ttc tgg aaa tct gac ttg gtt cgc ggt     2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca     2619
Glu Asn Asp Tyr Val Thr Phe Asp Phe Tyr Leu Asp Pro Val Arg Ala
                630                 635                 640 aca gaa ggc gca atg aat atc aat tta gta ttc cag cca cct act aac     2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa     2715
Gly Tyr Trp Val Gln Ala Pro Lys Thr Tyr Thr Ile Asn Phe Asp Glu
        660                 665                 670 tta gag gaa gcg aat caa gta aat ggt tta tat cac tat gaa gtg aaa     2763
Leu Glu Glu Ala Asn Gln Val Asn Gly Leu Tyr His Tyr Glu Val Lys
    675                 680                 685 att aac gta aga gat att aca aac att caa gat gac acg tta cta cgt     2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga     2859
Asn Met Met Ile Ile Phe Ala Asp Val Glu Ser Asp Phe Ala Gly Arg
                710                 715                 720 gtc ttt gta gat aat gtt cgt ttt gag ggg gct gct act act gag ccg     2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat     2955
Val Glu Pro Glu Pro Val Asp Pro Gly Glu Glu Thr Pro Pro Val Asp
        740                 745                 750 gag aag gaa gcg aaa aaa gaa caa aaa gaa gag aaa gaa gag aaa         3003
Glu Lys Glu Ala Lys Lys Glu Gln Lys Glu Ala Lys Glu Glu Lys
    755                 760                 765 gaa gca gta aaa gaa gaa aag aaa gaa gct aaa gaa gaa aag aaa gca     3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct    3105
Ile Lys Asn Glu Ala Thr Lys Lys
                790 aaaggtctga tgcagatctt ttagataacc ttttttttgca taactggaca tagaatggtt  3165 attaaagaaa gcaaggtgtt tatacgatat taaaaggta gcgattttaa attgaaacct    3225 ttaataatgt cttgtgatag aatgatgaag taatttaaga gggggaaacg aagtgaaaac   3285 ggaaatttct agtagaagaa aaacagacca agaaatactg caagctt                3332

<210> SEQ ID NO 4
<211> LENGTH: 822
<212> TYPE: PRT
<213> ORGANISM: Bacillus sp. KSM-64

<400> SEQUENCE: 4

Met Met Leu Arg Lys Lys Thr Lys Gln Leu Ile Ser Ser Ile Leu Ile
            -25                 -20                 -15

Leu Val Leu Leu Ser Leu Phe Pro Thr Ala Leu Ala Ala Glu Gly
        -10                  -5                 -1   1

Asn Thr Arg Glu Asp Asn Phe Lys His Leu Leu Gly Asn Asp Asn Val
        5                   10                  15

Lys Arg Pro Ser Glu Ala Gly Ala Leu Gln Leu Gln Glu Val Asp Gly
```

```
            20                  25                  30                  35
        Gln Met Thr Leu Val Asp Gln His Gly Glu Lys Ile Gln Leu Arg Gly
                            40                  45                  50
        Met Ser Thr His Gly Leu Gln Trp Phe Pro Glu Ile Leu Asn Asp Asn
                    55                  60                  65
        Ala Tyr Lys Ala Leu Ala Asn Asp Trp Glu Ser Asn Met Ile Arg Leu
                70                  75                  80
        Ala Met Tyr Val Gly Glu Asn Gly Tyr Ala Ser Asn Pro Glu Leu Ile
            85                  90                  95
        Lys Ser Arg Val Ile Lys Gly Ile Asp Leu Ala Ile Glu Asn Asp Met
        100                 105                 110                 115
        Tyr Val Ile Val Asp Trp His Val His Ala Pro Gly Asp Pro Arg Asp
                        120                 125                 130
        Pro Val Tyr Ala Gly Ala Glu Asp Phe Phe Arg Asp Ile Ala Ala Leu
                    135                 140                 145
        Tyr Pro Asn Asn Pro His Ile Ile Tyr Glu Leu Ala Asn Glu Pro Ser
                150                 155                 160
        Ser Asn Asn Asn Gly Gly Ala Gly Ile Pro Asn Asn Glu Glu Gly Trp
            165                 170                 175
        Asn Ala Val Lys Glu Tyr Ala Asp Pro Ile Val Glu Met Leu Arg Asp
        180                 185                 190                 195
        Ser Gly Asn Ala Asp Asp Asn Ile Ile Ile Val Gly Ser Pro Asn Trp
                        200                 205                 210
        Ser Gln Arg Pro Asp Leu Ala Ala Asp Asn Pro Ile Asp Asp His His
                    215                 220                 225
        Thr Met Tyr Thr Val His Phe Tyr Thr Gly Ser His Ala Ala Ser Thr
                230                 235                 240
        Glu Ser Tyr Pro Pro Glu Thr Pro Asn Ser Glu Arg Gly Asn Val Met
            245                 250                 255
        Ser Asn Thr Arg Tyr Ala Leu Glu Asn Gly Val Ala Val Phe Ala Thr
        260                 265                 270                 275
        Glu Trp Gly Thr Ser Gln Ala Asn Gly Asp Gly Gly Pro Tyr Phe Asp
                        280                 285                 290
        Glu Ala Asp Val Trp Ile Glu Phe Leu Asn Glu Asn Asn Ile Ser Trp
                    295                 300                 305
        Ala Asn Trp Ser Leu Thr Asn Lys Asn Glu Val Ser Gly Ala Phe Thr
                310                 315                 320
        Pro Phe Glu Leu Gly Lys Ser Asn Ala Thr Ser Leu Asp Pro Gly Pro
            325                 330                 335
        Asp Gln Val Trp Val Pro Glu Glu Leu Ser Leu Ser Gly Glu Tyr Val
        340                 345                 350                 355
        Arg Ala Arg Ile Lys Gly Val Asn Tyr Glu Pro Ile Asp Arg Thr Lys
                        360                 365                 370
        Tyr Thr Lys Val Leu Trp Asp Phe Asn Asp Gly Thr Lys Gln Gly Phe
                    375                 380                 385
        Gly Val Asn Gly Asp Ser Pro Val Glu Asp Val Val Ile Glu Asn Glu
                390                 395                 400
        Ala Gly Ala Leu Lys Leu Ser Gly Leu Asp Ala Ser Asn Asp Val Ser
            405                 410                 415
        Glu Gly Asn Tyr Trp Ala Asn Ala Arg Leu Ser Ala Asp Gly Trp Gly
        420                 425                 430                 435
        Lys Ser Val Asp Ile Leu Gly Ala Glu Lys Leu Thr Met Asp Val Ile
                        440                 445                 450
```

```
Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
        470                 475                 480

Asn Phe Val Pro Leu Gly Asp Lys Phe Lys Ala Glu Leu Thr Ile Thr
485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
                520                 525                 530

Val Ile Tyr Leu Asp Asn Ile Lys Val Ile Gly Thr Glu Val Glu Ile
            535                 540                 545

Pro Val Val His Asp Pro Lys Gly Glu Ala Val Leu Pro Ser Val Phe
        550                 555                 560

Glu Asp Gly Thr Arg Gln Gly Trp Asp Trp Ala Gly Glu Ser Gly Val
565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
                600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
        630                 635                 640

Gly Ala Met Asn Ile Asn Leu Val Phe Gln Pro Pro Thr Asn Gly Tyr
645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
                680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
        710                 715                 720

Val Asp Asn Val Arg Phe Glu Gly Ala Ala Thr Thr Glu Pro Val Glu
725                 730                 735

Pro Glu Pro Val Asp Pro Gly Glu Glu Thr Pro Pro Val Asp Glu Lys
740                 745                 750                 755

Glu Ala Lys Lys Glu Gln Lys Glu Ala Glu Lys Glu Lys Glu Lys Ala
                760                 765                 770

Val Lys Glu Glu Lys Lys Glu Ala Lys Glu Glu Lys Lys Ala Ile Lys
            775                 780                 785

Asn Glu Ala Thr Lys Lys
            790

<210> SEQ ID NO 5
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
```

```
<221> NAME/KEY: mat_peptide
<222> LOCATION: (660)..(3044)

<400> SEQUENCE: 5
gatttgccga tgcaacaggc ttatatttag aggaaatttc ttttttaaatt gaatacggaa    60 taaaatcagg taaacaggtc ctgatttttat ttttttgagt ttttttagaga actgaagatt   120 gaaataaaag tagaagacaa aggacataag aaaattgcat tagtttttaat tatagaaaac   180 gccttttttat aattatttat acctagaacg aaaatactgt ttcgaaagcg gtttactata   240
aaaccttata ttccggctct ttttttaaaac agggggtaaa aattcactct agtattctaa   300
tttcaacatg ctataataaa tttgtaagac gcaatatgca tctctttttt tacgatatat   360
gtaagcggtt aaccttgtgc tatatgccga tttaggaagg ggggtagatt gagtcaagta   420
gtaataatat agataactta taagttgttg agaagcagga gagcatctgg gttactcaca   480
agttttttta aaactttaac gaaagcactt tcggtaatgc ttatgaattt agctatttga   540
ttcaattact ttaaaaatat ttaggaggta at atg atg tta aga aag aaa aca    593
                                   Met Met Leu Arg Lys Lys Thr
                                   -25 aag cag ttg att tct tcc att ctt att tta gtt tta ctt cta tct tta    641
Lys Gln Leu Ile Ser Ser Ile Leu Ile Leu Val Leu Leu Leu Ser Leu
        -20              -15                  -10 ttt ccg gca gct ctt gca gca gaa gga aac act cgt gaa gac aat ttt    689
Phe Pro Ala Ala Leu Ala Ala Glu Gly Asn Thr Arg Glu Asp Asn Phe
    -5           -1  1                   5                    10 aaa cat tta tta ggt aat gac aat gtt aaa cgc cct tct gag gct ggc    737
Lys His Leu Leu Gly Asn Asp Asn Val Lys Arg Pro Ser Glu Ala Gly
15              20                  25 gca tta caa tta caa gaa gtc gat gga caa atg aca tta gta gat caa    785
Ala Leu Gln Leu Gln Glu Val Asp Gly Gln Met Thr Leu Val Asp Gln
            30                  35                  40 cat gga gaa aaa att caa tta cgt gga atg agt aca cac gga tta cag    833
His Gly Glu Lys Ile Gln Leu Arg Gly Met Ser Thr His Gly Leu Gln
        45                  50                  55 tgg ttt cct gag atc ttg aat gat aac gca tac aaa gct ctt tct aac    881
Trp Phe Pro Glu Ile Leu Asn Asp Asn Ala Tyr Lys Ala Leu Ser Asn
60                  65                  70 gat tgg gat tcc aat atg att cgt ctt gct atg tat gta ggt gaa aat    929
Asp Trp Asp Ser Asn Met Ile Arg Leu Ala Met Tyr Val Gly Glu Asn
75              80                  85                  90 ggg tac gct aca aac cct gag tta atc aaa caa aga gtg att gat gga    977
Gly Tyr Ala Thr Asn Pro Glu Leu Ile Lys Gln Arg Val Ile Asp Gly
                95                 100                 105 att gag tta gcg att gaa aat gac atg tat gtt att gtt gac tgg cat   1025
Ile Glu Leu Ala Ile Glu Asn Asp Met Tyr Val Ile Val Asp Trp His
            110                 115                 120 gtt cat gcg cca ggt gat cct aga gat cct gtt tat gca ggt gct aaa   1073
Val His Ala Pro Gly Asp Pro Arg Asp Pro Val Tyr Ala Gly Ala Lys
        125                 130                 135 gat ttc ttt aga gaa att gca gct tta tac cct aat aat cca cac att   1121
Asp Phe Phe Arg Glu Ile Ala Ala Leu Tyr Pro Asn Asn Pro His Ile
140                 145                 150 att tat gag tta gcg aat gag ccg agt agt aat aat ggt gga gca       1169
Ile Tyr Glu Leu Ala Asn Glu Pro Ser Ser Asn Asn Gly Gly Ala
155                 160                 165                 170 ggg att ccg aat aac gaa gaa ggt tgg aaa gcg gta aaa gaa tat gct   1217
Gly Ile Pro Asn Asn Glu Glu Gly Trp Lys Ala Val Lys Glu Tyr Ala
                175                 180                 185
```

```
gat cca att gta gaa atg tta cgt aaa agc ggt aat gca gat gac aac       1265
Asp Pro Ile Val Glu Met Leu Arg Lys Ser Gly Asn Ala Asp Asp Asn
        190                 195                 200 att atc att gtt ggt agt cca aac tgg agt cag cgt ccg gac tta gca       1313
Ile Ile Ile Val Gly Ser Pro Asn Trp Ser Gln Arg Pro Asp Leu Ala
            205                 210                 215 gct gat aat cca att gat gat cac cat aca atg tat act gtt cac ttc       1361
Ala Asp Asn Pro Ile Asp Asp His His Thr Met Tyr Thr Val His Phe
220                 225                 230 tac act ggt tca cat gct gct tca act gaa agc tat ccg tct gaa act       1409
Tyr Thr Gly Ser His Ala Ala Ser Thr Glu Ser Tyr Pro Ser Glu Thr
235                 240                 245                 250 cct aac tct gaa aga gga aac gta atg agt aac act cgt tat gcg tta       1457
Pro Asn Ser Glu Arg Gly Asn Val Met Ser Asn Thr Arg Tyr Ala Leu
                255                 260                 265 gaa aac gga gta gcg gta ttt gca aca gag tgg gga acg agt caa gct       1505
Glu Asn Gly Val Ala Val Phe Ala Thr Glu Trp Gly Thr Ser Gln Ala
            270                 275                 280 agt gga gac ggt ggt cct tac ttt gat gaa gca gat gta tgg att gaa       1553
Ser Gly Asp Gly Gly Pro Tyr Phe Asp Glu Ala Asp Val Trp Ile Glu
        285                 290                 295 ttt tta aat gaa aac aac att agc tgg gct aac tgg tct tta acg aat       1601
Phe Leu Asn Glu Asn Asn Ile Ser Trp Ala Asn Trp Ser Leu Thr Asn
300                 305                 310 aaa aat gaa gta tct ggt gca ttt aca cca ttc gag tta ggt aag tct       1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa       1697
Asn Ala Thr Asn Leu Asp Pro Gly Pro Asp His Val Trp Ala Pro Glu
                335                 340                 345 gaa tta agt ctt tct gga gaa tat gta cgt gct cgt att aaa ggt gtg       1745
Glu Leu Ser Leu Ser Gly Glu Tyr Val Arg Ala Arg Ile Lys Gly Val
            350                 355                 360 aac tat gag cca atc gac cgt aca aaa tac acg aaa gta ctt tgg gac       1793
Asn Tyr Glu Pro Ile Asp Arg Thr Lys Tyr Thr Lys Val Leu Trp Asp
        365                 370                 375 ttt aat gat gga acg aag caa gga ttt gga gtg aat tcg gat tct cca       1841
Phe Asn Asp Gly Thr Lys Gln Gly Phe Gly Val Asn Ser Asp Ser Pro
380                 385                 390 aat aaa gaa ctt att gca gtt gat aat gaa aac aac act ttg aaa gtt       1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct       1937
Ser Gly Leu Asp Val Ser Asn Asp Val Ser Asp Gly Asn Phe Trp Ala
                415                 420                 425 aat gct cgt ctt tct gcc aac ggt tgg gga aaa agt gtt gat att tta       1985
Asn Ala Arg Leu Ser Ala Asn Gly Trp Gly Lys Ser Val Asp Ile Leu
            430                 435                 440 ggt gct gag aag ctt aca atg gat gtt att gtt gat gaa cca acg acg       2033
Gly Ala Glu Lys Leu Thr Met Asp Val Ile Val Asp Glu Pro Thr Thr
        445                 450                 455 gta gct att gcg gcg att cca caa agt agt aaa agt gga tgg gca aat       2081
Val Ala Ile Ala Ala Ile Pro Gln Ser Ser Lys Ser Gly Trp Ala Asn
460                 465                 470 cca gag cgt gct gtt cga gtg aac gcg gaa gat ttt gtc cag caa acg       2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct       2177
Asp Gly Lys Tyr Lys Ala Gly Leu Thr Ile Thr Gly Glu Asp Ala Pro
                495                 500                 505
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| aac   | cta   | aaa   | aat   | atc   | gct   | ttt   | cat   | gaa   | gaa   | gat   | aac   | aat   | atg   | aac   | aac   | 2225 |
| Asn   | Leu   | Lys   | Asn   | Ile   | Ala   | Phe   | His   | Glu   | Glu   | Asp   | Asn   | Asn   | Met   | Asn   | Asn   |      |
|       |       |       |       | 510   |       |       |       |       | 515   |       |       |       |       | 520   |       |      |
| atc   | att   | ctg   | ttc   | gtg   | gga   | act   | gat   | gca   | gct   | gac   | gtt   | att   | tac   | tta   | gat   | 2273 |
| Ile   | Ile   | Leu   | Phe   | Val   | Gly   | Thr   | Asp   | Ala   | Ala   | Asp   | Val   | Ile   | Tyr   | Leu   | Asp   |      |
|       |       |       |       | 525   |       |       |       |       | 530   |       |       |       |       | 535   |       |      |
| aac   | att   | aaa   | gta   | att   | gga   | aca   | gaa   | gtt   | gaa   | att   | cca   | gtt   | gtt   | cat   | gat   | 2321 |
| Asn   | Ile   | Lys   | Val   | Ile   | Gly   | Thr   | Glu   | Val   | Glu   | Ile   | Pro   | Val   | Val   | His   | Asp   |      |
|       |       |       |       | 540   |       |       |       |       | 545   |       |       |       |       | 550   |       |      |
| cca   | aaa   | gga   | gaa   | gct   | gtt   | ctt   | cct   | tct   | gtt   | ttt   | gaa   | gac   | ggt   | aca   | cgt   | 2369 |
| Pro   | Lys   | Gly   | Glu   | Ala   | Val   | Leu   | Pro   | Ser   | Val   | Phe   | Glu   | Asp   | Gly   | Thr   | Arg   |      |
| 555   |       |       |       |       | 560   |       |       |       |       | 565   |       |       |       |       | 570   |      |
| caa   | ggt   | tgg   | gac   | tgg   | gct   | gga   | gag   | tct   | ggt   | gtg   | aaa   | aca   | gct   | tta   | aca   | 2417 |
| Gln   | Gly   | Trp   | Asp   | Trp   | Ala   | Gly   | Glu   | Ser   | Gly   | Val   | Lys   | Thr   | Ala   | Leu   | Thr   |      |
|       |       |       |       | 575   |       |       |       |       | 580   |       |       |       |       | 585   |       |      |
| att   | gaa   | gaa   | gca   | aac   | ggt   | tct   | aac   | gcg   | tta   | tca   | tgg   | gaa   | ttt   | gga   | tat   | 2465 |
| Ile   | Glu   | Glu   | Ala   | Asn   | Gly   | Ser   | Asn   | Ala   | Leu   | Ser   | Trp   | Glu   | Phe   | Gly   | Tyr   |      |
|       |       |       |       | 590   |       |       |       |       | 595   |       |       |       |       | 600   |       |      |
| cca   | gaa   | gta   | aaa   | cct   | agt   | gat   | aac   | tgg   | gca   | aca   | gct   | cca   | cgt   | tta   | gat   | 2513 |
| Pro   | Glu   | Val   | Lys   | Pro   | Ser   | Asp   | Asn   | Trp   | Ala   | Thr   | Ala   | Pro   | Arg   | Leu   | Asp   |      |
|       |       |       |       | 605   |       |       |       |       | 610   |       |       |       |       | 615   |       |      |
| ttc   | tgg   | aaa   | tct   | gac   | ttg   | gtt   | cgc   | ggt   | gag   | aat   | gat   | tat   | gta   | gct   | ttt   | 2561 |
| Phe   | Trp   | Lys   | Ser   | Asp   | Leu   | Val   | Arg   | Gly   | Glu   | Asn   | Asp   | Tyr   | Val   | Ala   | Phe   |      |
|       |       |       |       | 620   |       |       |       |       | 625   |       |       |       |       | 630   |       |      |
| gat   | ttc   | tat   | cta   | gat   | cca   | gtt   | cgt   | gca   | aca   | gaa   | ggc   | gca   | atg   | aat   | atc   | 2609 |
| Asp   | Phe   | Tyr   | Leu   | Asp   | Pro   | Val   | Arg   | Ala   | Thr   | Glu   | Gly   | Ala   | Met   | Asn   | Ile   |      |
| 635   |       |       |       |       | 640   |       |       |       |       | 645   |       |       |       |       | 650   |      |
| aat   | tta   | gta   | ttc   | cag   | cca   | cct   | act   | aac   | ggg   | tat   | tgg   | gta   | caa   | gca   | cca   | 2657 |
| Asn   | Leu   | Val   | Phe   | Gln   | Pro   | Pro   | Thr   | Asn   | Gly   | Tyr   | Trp   | Val   | Gln   | Ala   | Pro   |      |
|       |       |       |       | 655   |       |       |       |       | 660   |       |       |       |       | 665   |       |      |
| aaa   | acg   | tat   | acg   | att   | aac   | ttt   | gat   | gaa   | tta   | gag   | gaa   | gcg   | aat   | caa   | gta   | 2705 |
| Lys   | Thr   | Tyr   | Thr   | Ile   | Asn   | Phe   | Asp   | Glu   | Leu   | Glu   | Glu   | Ala   | Asn   | Gln   | Val   |      |
|       |       |       |       | 670   |       |       |       |       | 675   |       |       |       |       | 680   |       |      |
| aat   | ggt   | tta   | tat   | cac   | tat   | gaa   | gtg   | aaa   | att   | aac   | gta   | aga   | gat   | att   | aca   | 2753 |
| Asn   | Gly   | Leu   | Tyr   | His   | Tyr   | Glu   | Val   | Lys   | Ile   | Asn   | Val   | Arg   | Asp   | Ile   | Thr   |      |
|       |       |       |       | 685   |       |       |       |       | 690   |       |       |       |       | 695   |       |      |
| aac   | att   | caa   | gat   | gac   | acg   | tta   | cta   | cgt   | aac   | atg   | atg   | atc   | att   | ttt   | gca   | 2801 |
| Asn   | Ile   | Gln   | Asp   | Asp   | Thr   | Leu   | Leu   | Arg   | Asn   | Met   | Met   | Ile   | Ile   | Phe   | Ala   |      |
| 700   |       |       |       |       | 705   |       |       |       |       | 710   |       |       |       |       |       |      |
| gat   | gta   | gaa   | agt   | gac   | ttt   | gca   | ggg   | aga   | gtc   | ttt   | gta   | gat   | aat   | gtt   | cgt   | 2849 |
| Asp   | Val   | Glu   | Ser   | Asp   | Phe   | Ala   | Gly   | Arg   | Val   | Phe   | Val   | Asp   | Asn   | Val   | Arg   |      |
| 715   |       |       |       |       | 720   |       |       |       |       | 725   |       |       |       |       | 730   |      |
| ttt   | gag   | ggg   | gct   | gct   | act   | act   | gag   | ccg   | gtt   | gaa   | cca   | gag   | cca   | gtt   | gat   | 2897 |
| Phe   | Glu   | Gly   | Ala   | Ala   | Thr   | Thr   | Glu   | Pro   | Val   | Glu   | Pro   | Glu   | Pro   | Val   | Asp   |      |
|       |       |       |       | 735   |       |       |       |       | 740   |       |       |       |       | 745   |       |      |
| cct   | ggc   | gaa   | gag   | acg   | cca   | cct   | gtc   | gat   | gag   | aag   | gaa   | gcg   | aaa   | aaa   | gaa   | 2945 |
| Pro   | Gly   | Glu   | Glu   | Thr   | Pro   | Pro   | Val   | Asp   | Glu   | Lys   | Glu   | Ala   | Lys   | Lys   | Glu   |      |
|       |       |       |       | 750   |       |       |       |       | 755   |       |       |       |       | 760   |       |      |
| caa   | aaa   | gaa   | gca   | gag   | aaa   | gaa   | gag   | aaa   | gaa   | gca   | gta   | aaa   | gaa   | gaa   | aag   | 2993 |
| Gln   | Lys   | Glu   | Ala   | Glu   | Lys   | Glu   | Glu   | Lys   | Glu   | Ala   | Val   | Lys   | Glu   | Glu   | Lys   |      |
|       |       |       |       | 765   |       |       |       |       | 770   |       |       |       |       | 775   |       |      |
| aaa   | gaa   | gct   | aaa   | gaa   | gaa   | aag   | aaa   | gca   | gtc   | aaa   | aat   | gag   | gct   | aag   | aaa   | 3041 |
| Lys   | Glu   | Ala   | Lys   | Glu   | Glu   | Lys   | Lys   | Ala   | Val   | Lys   | Asn   | Glu   | Ala   | Lys   | Lys   |      |
|       |       |       |       | 780   |       |       |       |       | 785   |       |       |       |       | 790   |       |      |
| aaa   | taatctatta | aactagttat | agggttatct | aaaggtctga | tgtagatctt  |   |   |   |   |   |   |   |   |   |   | 3094 |
| Lys   |       |       |       |       |       |       |       |       |       |       |       |       |       |       |       |      |
| 795   |       |       |       |       |       |       |       |       |       |       |       |       |       |       |       |      | ttagataacc ttttctttgc ataactggac acagagttgt tattaaagaa agtaag    3150

<210> SEQ ID NO 6
<211> LENGTH: 824
<212> TYPE: PRT
<213> ORGANISM: Bacillus sp. KSM-S237

<400> SEQUENCE: 6

```
Met Met Leu Arg Lys Lys Thr Lys Gln Leu Ile Ser Ser Ile Leu Ile
        -25                 -20                 -15
Leu Val Leu Leu Leu Ser Leu Phe Pro Ala Ala Leu Ala Ala Glu Gly
        -10                  -5                  -1   1
Asn Thr Arg Glu Asp Asn Phe Lys His Leu Leu Gly Asn Asp Asn Val
          5                  10                  15
Lys Arg Pro Ser Glu Ala Gly Ala Leu Gln Leu Gln Glu Val Asp Gly
 20                  25                  30                  35
Gln Met Thr Leu Val Asp Gln His Gly Glu Lys Ile Gln Leu Arg Gly
             40                  45                  50
Met Ser Thr His Gly Leu Gln Trp Phe Pro Glu Ile Leu Asn Asp Asn
             55                  60                  65
Ala Tyr Lys Ala Leu Ser Asn Asp Trp Asp Ser Asn Met Ile Arg Leu
             70                  75                  80
Ala Met Tyr Val Gly Glu Asn Gly Tyr Ala Thr Asn Pro Glu Leu Ile
 85                  90                  95
Lys Gln Arg Val Ile Asp Gly Ile Glu Leu Ala Ile Glu Asn Asp Met
100                 105                 110                 115
Tyr Val Ile Val Asp Trp His Val His Ala Pro Gly Asp Pro Arg Asp
                120                 125                 130
Pro Val Tyr Ala Gly Ala Lys Asp Phe Phe Arg Glu Ile Ala Ala Leu
                135                 140                 145
Tyr Pro Asn Asn Pro His Ile Ile Tyr Glu Leu Ala Asn Glu Pro Ser
                150                 155                 160
Ser Asn Asn Asn Gly Gly Ala Gly Ile Pro Asn Asn Glu Glu Gly Trp
165                 170                 175
Lys Ala Val Lys Glu Tyr Ala Asp Pro Ile Val Glu Met Leu Arg Lys
180                 185                 190                 195
Ser Gly Asn Ala Asp Asp Asn Ile Ile Ile Val Gly Ser Pro Asn Trp
                200                 205                 210
Ser Gln Arg Pro Asp Leu Ala Ala Asp Asn Pro Ile Asp Asp His His
                215                 220                 225
Thr Met Tyr Thr Val His Phe Tyr Thr Gly Ser His Ala Ala Ser Thr
                230                 235                 240
Glu Ser Tyr Pro Ser Glu Thr Pro Asn Ser Glu Arg Gly Asn Val Met
245                 250                 255
Ser Asn Thr Arg Tyr Ala Leu Glu Asn Gly Val Ala Val Phe Ala Thr
260                 265                 270                 275
Glu Trp Gly Thr Ser Gln Ala Ser Gly Asp Gly Gly Pro Tyr Phe Asp
                280                 285                 290
Glu Ala Asp Val Trp Ile Glu Phe Leu Asn Glu Asn Asn Ile Ser Trp
                295                 300                 305
Ala Asn Trp Ser Leu Thr Asn Lys Asn Glu Val Ser Gly Ala Phe Thr
                310                 315                 320
Pro Phe Glu Leu Gly Lys Ser Asn Ala Thr Asn Leu Asp Pro Gly Pro
                325                 330                 335
Asp His Val Trp Ala Pro Glu Glu Leu Ser Leu Ser Gly Glu Tyr Val
340                 345                 350                 355
```

```
Arg Ala Arg Ile Lys Gly Val Asn Tyr Glu Pro Ile Asp Arg Thr Lys
            360                     365                 370

Tyr Thr Lys Val Leu Trp Asp Phe Asn Asp Gly Thr Lys Gln Gly Phe
            375                     380                 385

Gly Val Asn Ser Asp Ser Pro Asn Lys Glu Leu Ile Ala Val Asp Asn
            390                     395                 400

Glu Asn Asn Thr Leu Lys Val Ser Gly Leu Asp Val Ser Asn Asp Val
        405                     410                 415

Ser Asp Gly Asn Phe Trp Ala Asn Ala Arg Leu Ser Ala Asn Gly Trp
420                     425                     430             435

Gly Lys Ser Val Asp Ile Leu Gly Ala Glu Lys Leu Thr Met Asp Val
            440                     445                 450

Ile Val Asp Glu Pro Thr Thr Val Ala Ile Ala Ala Ile Pro Gln Ser
            455                     460                 465

Ser Lys Ser Gly Trp Ala Asn Pro Glu Arg Ala Val Arg Val Asn Ala
        470                     475                 480

Glu Asp Phe Val Gln Gln Thr Asp Gly Lys Tyr Lys Ala Gly Leu Thr
        485                     490                 495

Ile Thr Gly Glu Asp Ala Pro Asn Leu Lys Asn Ile Ala Phe His Glu
500                     505                     510             515

Glu Asp Asn Asn Met Asn Asn Ile Ile Leu Phe Val Gly Thr Asp Ala
                520                     525                 530

Ala Asp Val Ile Tyr Leu Asp Asn Ile Lys Val Ile Gly Thr Glu Val
                535                     540                 545

Glu Ile Pro Val Val His Asp Pro Lys Gly Glu Ala Val Leu Pro Ser
            550                     555                 560

Val Phe Glu Asp Gly Thr Arg Gln Gly Trp Asp Trp Ala Gly Glu Ser
        565                     570                 575

Gly Val Lys Thr Ala Leu Thr Ile Glu Glu Ala Asn Gly Ser Asn Ala
580                     585                     590             595

Leu Ser Trp Glu Phe Gly Tyr Pro Glu Val Lys Pro Ser Asp Asn Trp
                600                     605                 610

Ala Thr Ala Pro Arg Leu Asp Phe Trp Lys Ser Asp Leu Val Arg Gly
            615                     620                 625

Glu Asn Asp Tyr Val Ala Phe Asp Phe Tyr Leu Asp Pro Val Arg Ala
        630                     635                 640

Thr Glu Gly Ala Met Asn Ile Asn Leu Val Phe Gln Pro Pro Thr Asn
    645                     650                 655

Gly Tyr Trp Val Gln Ala Pro Lys Thr Tyr Thr Ile Asn Phe Asp Glu
660                     665                     670             675

Leu Glu Glu Ala Asn Gln Val Asn Gly Leu Tyr His Tyr Glu Val Lys
                680                     685                 690

Ile Asn Val Arg Asp Ile Thr Asn Ile Gln Asp Asp Thr Leu Leu Arg
            695                     700                 705

Asn Met Met Ile Ile Phe Ala Asp Val Glu Ser Asp Phe Ala Gly Arg
            710                     715                 720

Val Phe Val Asp Asn Val Arg Phe Glu Gly Ala Thr Thr Glu Pro
        725                     730                 735

Val Glu Pro Glu Pro Val Asp Pro Gly Glu Glu Thr Pro Pro Val Asp
740                     745                     750             755

Glu Lys Glu Ala Lys Lys Glu Gln Lys Glu Ala Glu Lys Glu Glu Lys
            760                     765                 770
```

-continued

```
Glu Ala Val Lys Glu Lys Lys Ala Lys Glu Gly Lys Lys Ala
            775                 780                 785

Val Lys Asn Glu Ala Lys Lys Lys
            790                 795

<210> SEQ ID NO 7
<211> LENGTH: 1531
<212> TYPE: DNA
<213> ORGANISM: Bacillus sp. KSM-K38
<220> FEATURE:
<221> NAME/KEY: CDS
<222> LOCATION: (1)..(1440)

<400> SEQUENCE: 7 gat gga ttg aac ggt acg atg atg cag tat tat gag tgg cat ttg gaa      48
Asp Gly Leu Asn Gly Thr Met Met Gln Tyr Tyr Glu Trp His Leu Glu
1               5                   10                  15 aac gac ggg cag cat tgg aat cgg ttg cac gat gat gcc gca gct ttg      96
Asn Asp Gly Gln His Trp Asn Arg Leu His Asp Asp Ala Ala Ala Leu
                20                  25                  30 agt gat gct ggt att aca gct att tgg att ccg cca gcc tac aaa ggt     144
Ser Asp Ala Gly Ile Thr Ala Ile Trp Ile Pro Pro Ala Tyr Lys Gly
            35                  40                  45 aat agt cag gcg gat gtt ggg tac ggt gca tac gat ctt tat gat tta     192
Asn Ser Gln Ala Asp Val Gly Tyr Gly Ala Tyr Asp Leu Tyr Asp Leu
        50                  55                  60 gga gag ttc aat caa aag ggt act gtt cga acg aaa tac gga act aag     240
Gly Glu Phe Asn Gln Lys Gly Thr Val Arg Thr Lys Tyr Gly Thr Lys
65                  70                  75                  80 gca cag ctt gaa cga gct att ggg tcc ctt aaa tct aat gat atc aat     288
Ala Gln Leu Glu Arg Ala Ile Gly Ser Leu Lys Ser Asn Asp Ile Asn
                85                  90                  95 gta tac gga gat gtc gtg atg aat cat aaa atg gga gct gat ttt acg     336
Val Tyr Gly Asp Val Val Met Asn His Lys Met Gly Ala Asp Phe Thr
                100                 105                 110 gag gca gtg caa gct gtt caa gta aat cca acg aat cgt tgg cag gat     384
Glu Ala Val Gln Ala Val Gln Val Asn Pro Thr Asn Arg Trp Gln Asp
            115                 120                 125 att tca ggt gcc tac acg att gat gcg tgg acg ggt ttc gac ttt tca     432
Ile Ser Gly Ala Tyr Thr Ile Asp Ala Trp Thr Gly Phe Asp Phe Ser
        130                 135                 140 ggg cgt aac aac gcc tat tca gat ttt aag tgg aga tgg ttc cat ttt     480
Gly Arg Asn Asn Ala Tyr Ser Asp Phe Lys Trp Arg Trp Phe His Phe
145                 150                 155                 160 aat ggt gtt gac tgg gat cag cgc tat caa gaa aat cat att ttc cgc     528
Asn Gly Val Asp Trp Asp Gln Arg Tyr Gln Glu Asn His Ile Phe Arg
                165                 170                 175 ttt gca aat acg aac tgg aac tgg cga gtg gat gaa gag aac ggt aat     576
Phe Ala Asn Thr Asn Trp Asn Trp Arg Val Asp Glu Glu Asn Gly Asn
                180                 185                 190 tat gat tac ctg tta gga tcg aat atc gac ttt agt cat cca gaa gta     624
Tyr Asp Tyr Leu Leu Gly Ser Asn Ile Asp Phe Ser His Pro Glu Val
            195                 200                 205 caa gat gag ttg aag gat tgg ggt agc tgg ttt acc gat gag tta gat     672
Gln Asp Glu Leu Lys Asp Trp Gly Ser Trp Phe Thr Asp Glu Leu Asp
        210                 215                 220 ttg gat ggt tat cgt tta gat gct att aaa cat att cca ttc tgg tat     720
Leu Asp Gly Tyr Arg Leu Asp Ala Ile Lys His Ile Pro Phe Trp Tyr
225                 230                 235                 240 aca tct gat tgg gtt cgg cat cag cgc aac gaa gca gat caa gat tta     768
Thr Ser Asp Trp Val Arg His Gln Arg Asn Glu Ala Asp Gln Asp Leu
```

```
                      245                 250                 255
ttt gtc gta ggg gaa tat tgg aag gat gac gta ggt gct ctc gaa ttt      816
Phe Val Val Gly Glu Tyr Trp Lys Asp Asp Val Gly Ala Leu Glu Phe
             260                 265                 270 tat tta gat gaa atg aat tgg gag atg tct cta ttc gat gtt cca ctt      864
Tyr Leu Asp Glu Met Asn Trp Glu Met Ser Leu Phe Asp Val Pro Leu
             275                 280                 285 aat tat aat ttt tac cgg gct tca caa caa ggt gga agc tat gat atg      912
Asn Tyr Asn Phe Tyr Arg Ala Ser Gln Gln Gly Gly Ser Tyr Asp Met
         290                 295                 300 cgt aat att tta cga gga tct tta gta gaa gcg cat ccg atg cat gca      960
Arg Asn Ile Leu Arg Gly Ser Leu Val Glu Ala His Pro Met His Ala
305                 310                 315                 320 gtt acg ttt gtt gat aat cat gat act cag cca ggg gag tca tta gag     1008
Val Thr Phe Val Asp Asn His Asp Thr Gln Pro Gly Glu Ser Leu Glu
                 325                 330                 335 tca tgg gtt gct gat tgg ttt aag cca ctt gct tat gcg aca att ttg     1056
Ser Trp Val Ala Asp Trp Phe Lys Pro Leu Ala Tyr Ala Thr Ile Leu
             340                 345                 350 acg cgt gaa ggt ggt tat cca aat gta ttt tac ggt gat tac tat ggg     1104
Thr Arg Glu Gly Gly Tyr Pro Asn Val Phe Tyr Gly Asp Tyr Tyr Gly
         355                 360                 365 att cct aac gat aac att tca gct aaa aaa gat atg att gat gag ctg     1152
Ile Pro Asn Asp Asn Ile Ser Ala Lys Lys Asp Met Ile Asp Glu Leu
     370                 375                 380 ctt gat gca cgt caa aat tac gca tat ggc acg cag cat gac tat ttt     1200
Leu Asp Ala Arg Gln Asn Tyr Ala Tyr Gly Thr Gln His Asp Tyr Phe
385                 390                 395                 400 gat cat tgg gat gtt gta gga tgg act agg gaa gga tct tcc tcc aga     1248
Asp His Trp Asp Val Val Gly Trp Thr Arg Glu Gly Ser Ser Ser Arg
                 405                 410                 415 cct aat tca ggc ctt gcg act att atg tcg aat gga cct ggt ggt tcc     1296
Pro Asn Ser Gly Leu Ala Thr Ile Met Ser Asn Gly Pro Gly Gly Ser
             420                 425                 430 aag tgg atg tat gta gga cgt cag aat gca gga caa aca tgg aca gat     1344
Lys Trp Met Tyr Val Gly Arg Gln Asn Ala Gly Gln Thr Trp Thr Asp
         435                 440                 445 tta act ggt aat aac gga gcg tcc gtt aca att aat ggc gat gga tgg     1392
Leu Thr Gly Asn Asn Gly Ala Ser Val Thr Ile Asn Gly Asp Gly Trp
     450                 455                 460 ggc gaa ttc ttt acg aat gga gga tct gta tcc gtg tac gtg aac caa     1440
Gly Glu Phe Phe Thr Asn Gly Gly Ser Val Ser Val Tyr Val Asn Gln
465                 470                 475                 480 taacaaaaag ccttgagaag ggattcctcc ctaactcaag ctttctttta tgtcgcttag   1500
ctttacgctt ctacgacttt gaagcttggg g                                  1531

<210> SEQ ID NO 8
<211> LENGTH: 480
<212> TYPE: PRT
<213> ORGANISM: Bacillus sp. KSM-K38

<400> SEQUENCE: 8

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45
```

-continued

Asn Ser Gln Ala Asp Val Gly Tyr Gly Ala Tyr Asp Leu Tyr Asp Leu
    50                  55                  60
Gly Glu Phe Asn Gln Lys Gly Thr Val Arg Thr Lys Tyr Gly Thr Lys
65                  70                  75                  80
Ala Gln Leu Glu Arg Ala Ile Gly Ser Leu Lys Ser Asn Asp Ile Asn
                85                  90                  95
Val Tyr Gly Asp Val Val Met Asn His Lys Met Gly Ala Asp Phe Thr
            100                 105                 110
Glu Ala Val Gln Ala Val Gln Val Asn Pro Thr Asn Arg Trp Gln Asp
        115                 120                 125
Ile Ser Gly Ala Tyr Thr Ile Asp Ala Trp Thr Gly Phe Asp Phe Ser
130                 135                 140
Gly Arg Asn Asn Ala Tyr Ser Asp Phe Lys Trp Arg Trp Phe His Phe
145                 150                 155                 160
Asn Gly Val Asp Trp Asp Gln Arg Tyr Gln Glu Asn His Ile Phe Arg
                165                 170                 175
Phe Ala Asn Thr Asn Trp Asn Trp Arg Val Asp Glu Glu Asn Gly Asn
            180                 185                 190
Tyr Asp Tyr Leu Leu Gly Ser Asn Ile Asp Phe Ser His Pro Glu Val
        195                 200                 205
Gln Asp Glu Leu Lys Asp Trp Gly Ser Trp Phe Thr Asp Glu Leu Asp
210                 215                 220
Leu Asp Gly Tyr Arg Leu Asp Ala Ile Lys His Ile Pro Phe Trp Tyr
225                 230                 235                 240
Thr Ser Asp Trp Val Arg His Gln Arg Asn Glu Ala Asp Gln Asp Leu
                245                 250                 255
Phe Val Val Gly Glu Tyr Trp Lys Asp Asp Val Gly Ala Leu Glu Phe
            260                 265                 270
Tyr Leu Asp Glu Met Asn Trp Glu Met Ser Leu Phe Asp Val Pro Leu
        275                 280                 285
Asn Tyr Asn Phe Tyr Arg Ala Ser Gln Gln Gly Gly Ser Tyr Asp Met
290                 295                 300
Arg Asn Ile Leu Arg Gly Ser Leu Val Glu Ala His Pro Met His Ala
305                 310                 315                 320
Val Thr Phe Val Asp Asn His Asp Thr Gln Pro Gly Glu Ser Leu Glu
                325                 330                 335
Ser Trp Val Ala Asp Trp Phe Lys Pro Leu Ala Tyr Ala Thr Ile Leu
            340                 345                 350
Thr Arg Glu Gly Gly Tyr Pro Asn Val Phe Tyr Gly Asp Tyr Tyr Gly
        355                 360                 365
Ile Pro Asn Asp Asn Ile Ser Ala Lys Lys Asp Met Ile Asp Glu Leu
370                 375                 380
Leu Asp Ala Arg Gln Asn Tyr Ala Tyr Gly Thr Gln His Asp Tyr Phe
385                 390                 395                 400
Asp His Trp Asp Val Val Gly Trp Thr Arg Glu Gly Ser Ser Ser Arg
                405                 410                 415
Pro Asn Ser Gly Leu Ala Thr Ile Met Ser Asn Gly Pro Gly Gly Ser
            420                 425                 430
Lys Trp Met Tyr Val Gly Arg Gln Asn Ala Gly Gln Thr Trp Thr Asp
        435                 440                 445
Leu Thr Gly Asn Asn Gly Ala Ser Val Thr Ile Asn Gly Asp Gly Trp
450                 455                 460
Gly Glu Phe Phe Thr Asn Gly Gly Ser Val Ser Val Tyr Val Asn Gln

<210> SEQ ID NO 9
<211> LENGTH: 31
<212> TYPE: DNA
<213> ORGANISM: Artificial sequence
<220> FEATURE:
<223> OTHER INFORMATION: Oligonucleotide as PCR primer

<400> SEQUENCE: 9
aaagaattcg cttatattta gaggaaattt c                                31

<210> SEQ ID NO 10
<211> LENGTH: 33
<212> TYPE: DNA
<213> ORGANISM: Artificial sequence
<220> FEATURE:
<223> OTHER INFORMATION: Oligonucleotide as PCR primer

<400> SEQUENCE: 10
tttggatcca ttacctccta aatattttta aag                              33

<210> SEQ ID NO 11
<211> LENGTH: 32
<212> TYPE: DNA
<213> ORGANISM: Artificial sequence
<220> FEATURE:
<223> OTHER INFORMATION: Oligonucleotide as PCR primer

<400> SEQUENCE: 11
gaaaatactg tttactataa aaccttatat tc                               32

<210> SEQ ID NO 12
<211> LENGTH: 32
<212> TYPE: DNA
<213> ORGANISM: Artificial sequence
<220> FEATURE:
<223> OTHER INFORMATION: Oligonucleotide as PCR primer

<400> SEQUENCE: 12
gaatataagg ttttatagta aacagtattt tc                               32

<210> SEQ ID NO 13
<211> LENGTH: 30
<212> TYPE: DNA
<213> ORGANISM: Artificial sequence
<220> FEATURE:
<223> OTHER INFORMATION: Oligonucleotide as PCR primer

<400> SEQUENCE: 13 cttttttttac gatataccttt gtgctatatg                                30

<210> SEQ ID NO 14
<211> LENGTH: 30
<212> TYPE: DNA
<213> ORGANISM: Artificial sequence
<220> FEATURE:
<223> OTHER INFORMATION: Oligonucleotide as PCR primer

<400> SEQUENCE: 14
catatagcac aaggtatatc gtaaaaaaag                                  30

US 9,029,519 B2

MODIFIED PROMOTER

REFERENCE TO SEQUENCE LISTING SUBMITTED ELECTRONICALLY

The content of the electronically submitted substitute sequence listing, file name 2537_0650002SEQListing.txt; size 53,861 bytes; and date of creation Feb. 28, 2012, filed herewith, is incorporated herein by reference in its entirety.

FIELD THE INVENTION

The present invention relates to a modified promoter, to an expression vector and a transformant each containing the promoter, and to a method for producing a gene product of interest using the transformant.

BACKGROUND OF THE INVENTION

Through use of microorganisms, a variety of useful substances have been produced on an industrial scale, including foods such as alcoholic beverages, miso, and shoyu (soy source); and other substances such as amino acids, organic acids, nucleic-acid-related substances, antibiotics, sugars, lipids, and proteins. Such substances are useful in a wide range of fields such as foods, pharmaceuticals, and daily-use articles such as detergents and cosmetics, as well as raw materials for chemical products.

In such industrial production of useful substances by the mediation of microorganisms, enhancement in productivity is an important issue. One approach which has been employed for enhancing productivity is breeding, through a genetic technique such as mutation, a bacterium which produces a substance of interest. In recent years, accompanied with the development of microbial genetics and biotechnology, more effective methods based on a recombinant technique or the like have been focused for producing useful substances.

A number of studies have been conducted on promoters which are required for the transcription of genes. Regarding *Bacillus subtilis*, a promoter domain of an alkaline cellulase gene derived from *Bacillus* sp. KSM-64 strain (FERM BP-2886) (see, for example, Non-Patent Document 1), a promoter domain present on the upstream side of an alkaline cellulase gene derived from *Bacillus* sp. KSM-S237 strain (FERM BP-7875) (see, for example, Patent Document 1 and Non-Patent Document 2), and other promoter domains are employed as promoter domains which actively transcript a gene encoding a heterologous protein or polypeptide.

However, in order to reduce production cost in industrial production, there is demand for a promoter or a microorganism which realizes higher productivity.

Generally, a promoter domain has various sites relating to regulation of transcription. These sites play a role in promoting or suppressing expression of a gene by the mediation of external signals. For example, when a culture medium for microorganisms contains large amounts of catabolites such as glucose, the microorganisms utilize mainly the catabolites as carbon sources, and the expression of an enzyme for degrading higher-molecule sugar is suppressed. This phenomenon is called "catabolite repression," which has been observed in *E. coil*, *Bacillus*, etc. Catabolite repression in *Bacillus subtilis* is known to occur at the transcription level. The domain which is involved in catabolite repression in *Bacillus* is called "catabolite responsive element (cre)."

Non-Patent Document 3 discloses that catabolite repression may be increased or reduced by a point mutation in a catabolite repression operator domain in the *Bacillus subtilis*-derived α-amylase gene. Meanwhile, in a promoter in the *Bacillus subtilis*-derived endo-glucanase, there is a nucleotide sequence similar to that of the catabolite repression domain of α-amylase, which is called a "catabolite repression operator-like sequence" (Non-Patent Document 2). However, the actual role of the sequence has not been elucidated.

[Patent Document 1] JP-A-2000-210081
[Non-Patent Document 1] Sumitomo et al., Biosci. Biotech. Biochem., 59: 2172-2175, 1995
[Non-Patent Document 2] Hakamada et al., Biosci. Biotech. Biochem. 64: 2281-2289, 2000
[Non-Patent Document 3] Weickert & Chambliss, Proc. Natl. Acad. Sci. USA, 87: 6238-6242, 1990

DISCLOSURE OF THE INVENTION

The present invention is directed to a modified promoter, including a nucleotide sequence of a promoter derived from bacterium belonging to the genus *Bacillus* in which at least one nucleotide sequence selected from the following has been modified: a nucleotide sequence represented by SEQ ID NO: 1; a nucleotide sequence equivalent to the nucleotide sequence represented by SEQ ID NO: 1, except that one or a plurality of bases therein are substituted, deleted, added or inserted; and a nucleotide sequence having a sequence identity of 700 or more with respect to the nucleotide sequence represented by SEQ ID NO: 1.

The present invention is also directed to a method for producing a modified promoter, the method including modifying, in a promoter derived from bacterium belonging to the genus *Bacillus*, at least one nucleotide sequence selected from the following: a nucleotide sequence represented by SEQ ID NO: 1; a nucleotide sequence equivalent to the nucleotide sequence represented by SEQ ID NO: 1, except that one or a plurality of bases therein are substituted, deleted, added or inserted; and a nucleotide sequence having a sequence identity of 70% or more with respect to the nucleotide sequence represented by SEQ ID NO: 1.

The present invention is also directed to the above-mentioned modified promoter or a modified promoter produced by the above-mentioned method, wherein one or a plurality of bases therein are further substituted, deleted, added or inserted.

The present invention is also directed to an expression vector including the above-mentioned modified promoter or the modified promoter produced by the above-mentioned method.

The present invention is also directed to a transformant including the above-mentioned modified promoter or the modified promoter produced by the above-mentioned method.

The present invention is also directed to a method for producing a gene product of interest, the method includes employing the transformant.

In one embodiment, the nucleotide sequence having a sequence identity of 70% or more with respect to the nucleotide sequence represented by SEQ ID NO: 1 is a nucleotide sequence represented by SEQ ID NO: 2.

In another embodiment, the promoter derived from a bacterium belonging to the genus *Bacillus* is a promoter from *Bacillus subtilis* or a mutant strain of *Bacillus subtilis*.

In another embodiment, the promoter derived from a bacterium belonging to the genus *Bacillus* is: a promoter of an alkaline cellulase gene from *Bacillus* sp. KSM-64 strain (FERN BP-2886); a promoter of an alkaline cellulase gene from *Bacillus* sp. KSM-5237 strain (FERN BP-7875); or a promoter containing a nucleotide sequence which has a sequence identity of 700 or more with respect to the nucleotide sequence of any one of said promoters and having a cre-like sequence.

In another embodiment, the modification of the nucleotide sequences is deletion, substitution or addition of a base in the nucleotide sequences.

In another embodiment, the modified promoter is operably linked to the upstream of a gene encoding a gene product of interest.

DETAILED DESCRIPTION OF THE INVENTION

Figure 1:
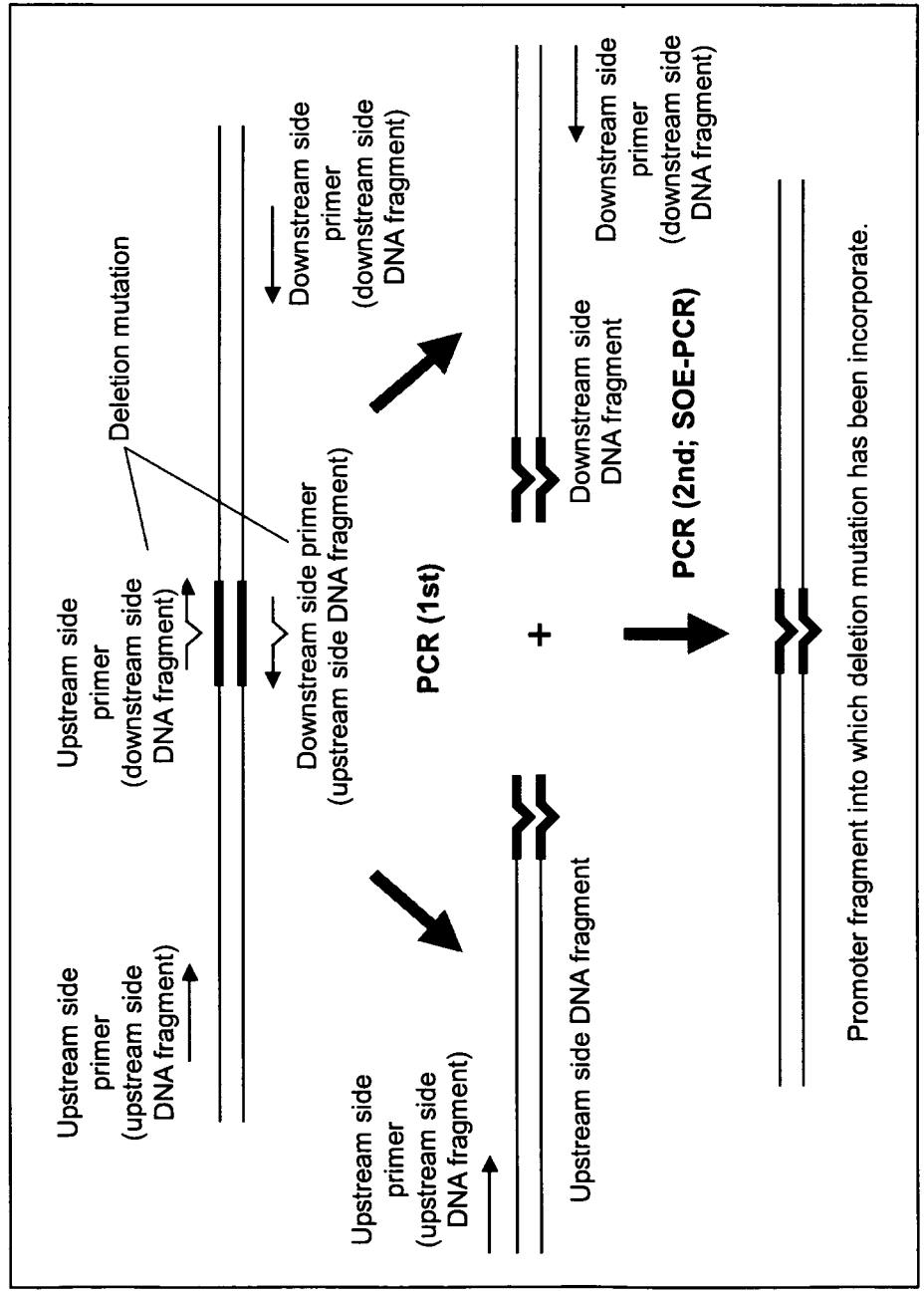
FIG. 1 A procedure for producing a mutated promoter having a deletion through the SOE-PCR method.

The present invention relates to provision of a modified promoter which enhances the gene transcription, an expression vector and a transformant each containing the promoter, and a method for producing a gene product of interest by use of the transformant.

The present inventors have found that a plurality of sequences which are similar to catabolite repression sequences in the promoter domain of a cellulase gene in a microorganism belonging to the genus *Bacillus*. The present inventors have also found that when the thus-found sequences were mutated, expression of the gene regulated by the promoter was considerably increased and productivity of the gene product encoded by the gene was enhanced.

The modified promoter of the present invention remarkably enhances the transcription amount of the gene which is linked to the downstream of the promoter. Thus, according to the present invention, a target gene product is yielded more efficiently.

In the present invention, sequence identity between amino acid sequences and that between nucleotide sequences are both determined through the Lipman-Pearson method (Science, 227, 1435 (1985)). Specifically, sequence identity is calculated through analysis by use of a homology analysis (search homology) program of genetic information processing software Genetyx-Win (Software Development Co., Ltd.), with the parameter ktup (unit size to compare) being set to 2.

Unless otherwise specified, the nucleotide sequence and base Nos. of *Bacillus subtilis* DNA used in the present specification are based on the *Bacillus subtilis* transcriptional factor retrieval site (http://dbtbs.hgc.jp/).

The modified promoter of the present invention is produced by modifying a nucleotide sequence similar to that of the catabolite responsive element (hereinafter referred to as "cre-like sequence") present in a polynucleotide encoding a promoter derived from a gene in a microorganism belonging to the genus *Bacillus* having the cre-like sequence. Examples of the cre-like sequence include a nucleotide sequence represented by SEQ ID NO: 1, and a nucleotide sequence equivalent to the nucleotide sequence represented by SEQ ID NO: 1, except that one or a plurality of bases therein are substituted, deleted, added or inserted. Examples of the cre-like sequence further include a nucleotide sequence having a sequence identity of 700 or more, preferably 800 or more, more preferably 900 or more with respect to the nucleotide sequence represented by SEQ ID NO: 1. As used herein, the term "a plurality of" refers to 1 to 6, preferably 1 to 3.

The method of substituting, deleting, adding or inserting a base is disclosed in, for example, Dieffenbach et al. (Cold Spring Harbor Laboratory Press, New York, 581-621, 1995). Through employment of this technique, one or a plurality of bases can be substituted, deleted, added, or inserted. Whether or not the sequence of interest is a cre-like sequence may be confirmed, for example, by observing enhanced expression of a target gene in the presence of a catabolite such as glucose when mutation is introduced in the sequence in a manner similar to that of the Examples described hereinbelow. Examples of the nucleotide sequence having a sequence identity of 70% or more with respect to the nucleotide sequence represented by SEQ ID NO: 1 include a nucleotide sequence represented by SEQ ID NO: 2. The nucleotide sequence represented by SEQ ID NO: 2 is equivalent to the nucleotide sequence represented by SEQ ID NO: 1, except that three bases therein have been substituted. Therefore, the nucleotide sequence represented by SEQ ID NO: has a homology of 76.9% with respect to the nucleotide sequence represented by SEQ ID NO: 1.

No particular limitation is imposed on the promoter derived from a bacterium belonging to the genus *Bacillus* from which the modified promoter of the present invention is produced, i.e., the parent promoter corresponding to the modified promoter of the present invention, so long as the parent promoter is a promoter which is derived from a bacterium belonging to the genus *Bacillus* and which has a cre-like sequence. The parent promoter is preferably derived from *Bacillus subtilis* or a mutant strain of *Bacillus subtilis*. Examples of preferred parent promoter include a promoter of an alkaline cellulase gene derived from *Bacillus* sp. KSM-64 strain (FERM BP-2886) (base Nos. 1 to 609 in SEQ ID NO: 3) and a promoter of an alkaline cellulase gene derived from *Bacillus* sp. KSM-S237 strain (FERM BP-7875) (base Nos. 1 to 572 in SEQ ID NO: 4). The nucleotide sequences represented by SEQ ID NO: 1 and 2 correspond to the nucleotide sequences of base Nos. 399 to 412 and 264 to 276, respectively, in the promoter of an alkaline cellulase gene from the KSM-64 strain which is represented by base Nos. 1 to 609 in SEQ ID NO: 3, and correspond to the nucleotide sequences of base Nos. 359 to 372 and 223 to 235, respectively, in the promoter of an alkaline cellulase gene from the KSM-5237 strain which is represented by base Nos. 1 to 572 in SEQ ID NO: 4.

Other examples of the parent promoter in the present invention include a promoter derived from a bacterium belonging to the genus *Bacillus* and having a cre-like sequence, which has: a nucleotide sequence equivalent to the nucleotide sequence of the promoter of the alkaline cellulase gene represented by SEQ ID NO: 3 or 4, except that one or a plurality of bases therein are substituted, deleted, added or inserted; or a nucleotide sequence having a sequence identity of 70% or more, preferably 80% or more, more preferably 90% or more, even more preferably 95% or more, yet more preferably 98% or more, with respect to the nucleotide sequence of the promoter of the alkaline cellulase gene represented by SEQ ID NO: 3 or 4. Whether or not the promoter has a cre-like sequence may be confirmed by determining the presence of a cre-like sequence in the nucleotide sequence of the promoter through sequencing, or by comparing the sequence of the promoter with that of the promoter of the alkaline cellulase gene represented by SEQ ID NO: 3 or 4 to identify the region corresponding to the cre-like sequence. The method of substituting, deleting, adding or inserting a base is disclosed in, for example, Dieffenbach et al. (Cold Spring Harbor Laboratory Press, New York, 581-621, 1995). Through employment of this technique, one or a plurality of bases can be substituted, deleted, added or inserted. The promoter sequence may be identified, for example, by observing expression of β-galactosidase when a LacZ gene has been introduced in a manner similar to that of the Examples described hereinbelow.

In the case where the parent promoter includes two or more of cre-like sequences, at least one nucleotide sequence of the cre-like sequences present in the parent promoter may be modified. In other words, one, two or more, or all of the cre-like sequences present in the parent promoter may be modified. For example, when the parent prompter has two cre-like sequences represented by SEQ ID NOs: 1 and 2, only the nucleotide sequence represented by SEQ ID NO: 1 or the nucleotide sequence represented by SEQ ID NO: 2 may be modified, or both of the two nucleotide sequences represented by SEQ ID NO: 1 and SEQ ID NO: 2 may be modified. Preferably, the two nucleotide sequences represented by SEQ ID NO: 1 and SEQ ID NO: 2 are modified.

In one embodiment, the modified promoter of the present invention is produced by modifying at least one cre-like sequence present in a promoter from *Bacillus subtilis* or a mutant strain of *Bacillus subtilis*.

In another embodiment, the modified promoter of the present invention is produced by modifying at least one of the cre-like sequence represented by base Nos. 264 to 276 and the cre-like sequence represented by base Nos. 399 to 412, in the promoter of an alkaline cellulase gene derived from KSM-64 strain (FERM BP-2886) (base Nos. 1 to 609 in SEQ ID NO: 3). Preferably, both the cre-like sequence represented by base Nos. 264 to 276 and the cre-like sequence represented by base Nos. 399 to 412 are modified.

In another embodiment, the modified promoter of the present invention is produced by modifying at least one of the cre-like sequence represented by base Nos. 223 to 235 and the cre-like sequence represented by base Nos. 359 to 372, in the promoter of an alkaline cellulase gene derived from *Bacillus* sp. KSM-S237 strain (FERM BP-7875) (base Nos. 1 to 572 in SEQ ID NO: 4). Preferably, both the cre-like sequence represented by base Nos. 223 to 235 and the cre-like sequence represented by base Nos. 359 to 372 are modified.

Examples of the modification of the nucleotide sequence of the cre-like sequence include deletion of a part of or the entirety of the bases in the nucleotide sequence, substitution of a part of or the entirety of the bases in the nucleotide sequence, and addition of a base at any position in the nucleotide sequence. As used herein the term "a part of the bases" refers to one or more bases, preferably three or more bases, more preferably 6 or more bases, even more preferably 10 or more bases. Deletion, substitution, or addition of a base may be performed through a method generally employed in the art, such as site-directed mutagenesis. The site-directed mutagenesis may be performed through the Kunkel method (Proc. Natl. Acad. Sci. USA., 82, 488, 1985), PCR, or the like.

Alternatively, the modified promoter of the present invention may be produced through the SOE (splicing by overlap extension)-PCR method (Gene, 77, 51, 1989), in which a base is deleted, substituted, or added in the nucleotide sequence of the cre-like sequence present in the promoter.

According to the SOE-PCR method, an upstream DNA fragment having a nucleotide sequence modification site at the downstream end, and a downstream DNA fragment having a nucleotide sequence modification site at the upstream end are prepared through the first PCR. In the case where a fragment in which a cre-like sequence has been deleted is prepared, a primer is designed such that the downstream side of the upstream DNA fragment and the upstream side of the downstream DNA fragment are mutually annealed, and a cre-like-sequence-deleted nucleotide sequence is provided (FIG. 1).

Subsequently, the second PCR is performed by use of the two DNA fragments prepared by the first PCR as templates, and the upstream primer of the upstream DNA fragment and the downstream primer of the DNA fragment. As a result, annealing occurs between the downstream end of the upstream DNA fragment and the upstream end of the downstream DNA fragment, whereby the two DNA fragments are linked to each other. Thus, a DNA fragment containing a promoter sequence in which a cre-like sequence has been deleted is produced (FIG. 1). In this case, when the primers employed in PCR are designed to have a restriction sequence, a promoter DNA fragment including restriction sequences at the ends is produced, and incorporated into a vector through the restriction enzyme method.

Similarly, when a primer is designed such that the downstream side of the upstream DNA fragment and the upstream side of the downstream DNA fragment are mutually annealed and that a nucleotide sequence including a cre-like sequence in which at least one base is substituted or added is prepared, there can be prepared a DNA fragment containing a promoter sequence in which at least one base of the cre-like sequence has been substituted or added.

In the modified promoter of the present invention, one or a plurality of bases may be further substituted, deleted, added or inserted, so long as the function of the promoter and the effect of enhancing expression of the gene of interest are maintained. The method of substituting, deleting, adding or inserting a base is disclosed in, for example, Dieffenbach et al. (Cold Spring Harbor Laboratory Press, New York, 581-621, 1995). Through employment of this technique, one or a plurality of bases can be substituted, deleted, added or inserted. Whether or not the modified promoter which has been further modified has promoter function and exhibits an effect of enhancing expression of a gene of interest may be confirmed, for example, by observing an effect of enhancing expression of a target gene in the presence of a catabolite such as glucose in a manner similar to that of the Examples described hereinbelow.

Through incorporation of the thus-prepared modified promoter of the present invention into an appropriate vector, the expression vector of the present invention can be produced. No particular limitation is imposed on the vector into which the modified promoter is incorporated, and vectors such as pDL2 and pMUTIN are preferred. Incorporation of a modified promoter into a vector may be performed in accordance with any methods generally employed in the art. For example, a vector is cleaved by means of restriction enzymes, and combined with a promoter having the above-produced restriction sequences at the ends, whereby the promoter is incorporated into the vector (restriction enzyme method).

In the expression vector of the present invention, the modified promoter of the present invention is operably linked to the upstream of the gene encoding a gene product of interest. Examples of the gene product of interest include protein, polypeptide and non-coding RNA. No particular limitation is imposed on the species of the protein and polypeptide, and the protein or the polypeptide includes enzymes for industrial uses such as detergents, foods, fiber, livestock feed, chemicals, medical care, and diagnosis, as well as physiologically active peptides. Examples of the enzyme for industrial uses include oxidoreductase, transferase, hydrolase, lyase, isomerase and ligase/synthetase. Genes of hydrolases such as cellulase, amylase and protease are preferred. Specific examples of the hydrolase include cellulase belonging to the family 5 as defined by the classification of polysaccharide hydrolases (Biochem. J., 280, 309, 1991). Among them, cellulases derived from microorganisms; for example, a microorganism belonging to the genus *Bacillus*, are preferred. More specific examples include an alkaline cellulase derived from *Bacillus* sp. KSM-64 strain (FERM BP-2886) consisting of an amino acid sequence represented by SEQ ID NO: 3, an alkaline cellulase derived from *Bacillus* sp. KSM-S237 strain (FERM BP-7875) consisting of an amino acid sequence represented by SEQ ID NO: 4, and cellulases consisting of an amino acid sequence having a sequence identity of 70% or more, preferably 80% or more, more preferably 90% or more, even more preferably 95% or more, yet more preferably 98% or more, with respect to the amino acid sequence represented by SEQ ID NO: 3 or 4.

Specific examples of the α-amylase include α-amylases derived from microorganisms. A liquefying α-amylase derived from a microorganism belonging to the genus *Bacillus* is preferred. More specific examples include an alkaline amylase derived from *Bacillus* sp. KSM-K38 strain (FERM BP-6946) consisting of an amino acid sequence represented by SEQ ID NO: 5 and amylases consisting of an amino acid sequence having a sequence identity of 70% or more, preferably 80% or more, more preferably 90% or more, even more preferably 95% or more, yet more preferably 98% or more, with respect to the amino acid sequence represented by SEQ ID NO: 5. Specific examples of the protease include serine protease and metalloprotease derived from a microorganism such as a microorganism belonging to the genus *Bacillus*.

Preferably, the aforementioned protein gene or polypeptide gene is operably linked to the region of the modified promoter of the present invention and to a secretion signal peptide region. For example, a structural gene of the target protein or polypeptide may be operably linked to a secretion signal peptide region of a cellulase gene derived from KSM-64 strain (FERM BP-2886) or KSM-S237 strain (FERM BP-7875). More specifically, a structural gene of the target protein or polypeptide may be operably linked to a nucleotide sequence represented by base Nos. 610 to 696 of SEQ ID NO: 3; a nucleotide sequence represented by base Nos. 573 to 659 of SEQ ID NO: 4; a DNA fragment consisting of a nucleotide sequence having a sequence identity of 70% or more, preferably 80% or more, more preferably 90% or more, even more preferably 95% or more, yet more preferably 98% or more, with respect to any of the above nucleotide sequences; or a DNA fragment equivalent to any of the nucleotide sequences, except that a part of a base or bases are deleted.

The non-coding RNA is an RNA which is not translated to protein after transcription from the corresponding DNA. Examples of the non-coding RNA include a non-translated region including a regulatory sequence, tRNA, rRNA, mRNA-type ncRNA (mRNA-like non-coding RNA), snRNA (small nuclear RNA), snoRNA (small nucleolar RNA), miRNA (microRNA), stRNA (small temporal RNA), and siRNA (short-interfering RNA). These non-coding RNAs are involved in various mechanisms of biological activity including regulation of cell expression, development, differentiation and others, and may be utilized in research, medical care, diagnosis, drug development, agriculture (e.g., breeding or pesticide production), fisheries, the livestock industry, and chemical production.

The modified promoter of the present invention and a gene encoding a gene product of interest or a secretion signal peptide region may be linked before incorporating them into a vector. Alternatively, the modified promoter of the present invention may be incorporated into a vector already containing a gene encoding a gene product of interest or the vector further containing a secretion signal peptide region.

As used herein, the term "operable linking" between the promoter and a gene, or between the promoter, a gene and a secretion signal refers to such a linkage that the promoter can induce transcription of the gene, or such a linkage that the protein encoded by the gene is secreted by the secretion signal. The procedure of "operable linking" between the promoter and a gene, or between the promoter, a gene and a secretion signal, is known to those skilled in the art.

Through incorporation of the produced expression vector of the present invention into a host microorganism by an ordinary transformation method, the transformant of the present invention is yielded. Alternatively, the transformant of the present invention may also be produced by constituting a DNA fragment in which an appropriate region homologous to the genome of the host microorganism is combined with a fragment prepared by linking the modified promoter of the present invention to a gene encoding a gene product of interest and optionally to a secretion signal peptide region; and directly incorporating the DNA fragment into the genome of the host microorganism through homologous recombination.

The transformant of the present invention may also be provided by incorporating the expression vector of the present invention into a host microorganism with an ordinary recombination technique.

A gene product of interest may be produced by use of the transformant of the present invention through the following procedure: inoculating the transformant strain to a medium containing an assimilable carbon source, nitrogen source and other essential ingredients; culturing the transformants through an ordinary culturing method; and subsequently collecting or purifying a gene product of interest. As described in the Examples hereinbelow, the transformant of the present invention exhibits higher productivity of a gene product of interest, as compared with a microorganism in which the cre-like sequence has not been modified.

EXAMPLES

The present invention will next be described in more detail by way of examples.

Example 1

Preparation of Modified Promoter Derived from Alkaline Cellulase Gene

A promoter DNA fragment derived from KSM-S237 cellulase (Hakamada et al., Biosci. Biotechnol. Biochem. 64, 2281-2289, 2000) was prepared by PCR. A fragment of promoter region in an alkaline cellulase gene DNA derived from *Bacillus* sp. KSM-S237 (base Nos. 1 to 572 of SEQ ID NO: 4), which has been incorporated in a shuttle vector pHY300PLK for *E. coli-Bacillus subtilis*, was used as a template. EcoRI_PS237 FW (SEQ ID NO: 6) and BamHI_PS237 RV (SEQ ID NO: 7) shown in Table 1 was used as primers. A promoter DNA fragment having an EcoRI-recognition site on the upstream side and a BamHI-recognition site on the downstream side was prepared by PCR using the template and the primers described above. Then, for preparing a mutant promoter DNA fragment in which a target sequence in the promoter DNA fragment has been deleted, PCRs were conducted using the fragment prepared through the above PCR as a template, and a primer set of Δcre1 FW (SEQ ID NO: 8) and BamHI_PS237 RV or a primer set of EcoRI_PS237 FW and Δcre1 RV (SEQ ID NO: 9), each shown in Table 1, thereby preparing fragments having, on the upstream side and the downstream side respectively, a region in which a target sequence has been deleted. The thus-obtained two fragments were combined to be used as a mixed template. PCR was conducted with the mixed template and a EcoRI_PS237 FW primer and a BamHI_PS237 RV primer to prepare a promoter sequence DNA fragment in which base residues 223 to 235 in the nucleotide sequence represented by SEQ ID NO: 4 have been deleted (Δcre1) (FIG. 1). In a similar manner, a promoter domain sequence DNA fragment in which base residues 359 to 372 in the nucleotide sequence represented by SEQ ID NO: 4 have been deleted (Δcre2) was prepared, by use of Δcre2 FW (SEQ ID NO: 10) instead of Δcre1 FW, and Δcre2 RV (SEQ ID NO: 11) instead of Δcre1 RV. Further PCRs were conducted using Δcre1 as a template, and a primer set of Δcre2 FW and BamHI_PS237 RV or a primer set of EcoRI_PS237 FW and Δcre2 RV. Using the two fragments thus-obtained as a mixed template, PCR was conducted with primers EcoRI_PS237 FW and BamHI_PS237 RV, thereby preparing a promoter sequence DNA fragment in which base residues 223 to 235 and 359 to 372 in the nucleotide sequence represented by SEQ ID NO: 4 have been deleted (Δcre1.2).

For amplifying a DNA fragment, PCR was conducted by means of a GeneAmp PCR System (product of Applied Biosystems) and by use of Pyrobest DNA Polymerase (Product of Takara Bio) and reagents attached thereto. The PCR solution (50 µL) was prepared so as to combine an appropriately diluted template DNA fragment (1 µL), each of a sense primer and an anti-sense primer (10 pmol each), and Pyrobest DNA Polymerase (2.5 U). PCR included 30 cycles of the 3-step thermal treatment (98° C. for 10 sec, 55° C. for 30 sec, and 72° C. for 1 to 5 min (about 1 min/kb, with adjusting in accordance with the target product) and reaction at 72° C. for 5 min.

TABLE 1

| Primer | Nucleotide sequence 5'→3' | SEQ ID NO: |
|---|---|---|
| EcoRI_PS237 FW | AAAGAATTCGCTTATATTTAGAGGAAATTTC | 6 |
| BamHI_PS237 RV | TTTGGATCCATTACCTCCTAAATATTTTTAAAG | 7 |
| Δcre1 FW | GAAAATACTGTTTACTATAAAACCTTATATTC | 8 |
| Δcre1 RV | GAATATAAGGTTTTATAGTAAACAGTATTTTC | 9 |
| Δcre2 FW | CTTTTTTTACGATATACCTTGTGCTATATG | 10 |
| Δcre2 RV | CATATAGCACAAGGTATATCGTAAAAAAAG | 11 |

Example 2

Preparation of Expression Vectors

Figure 2:
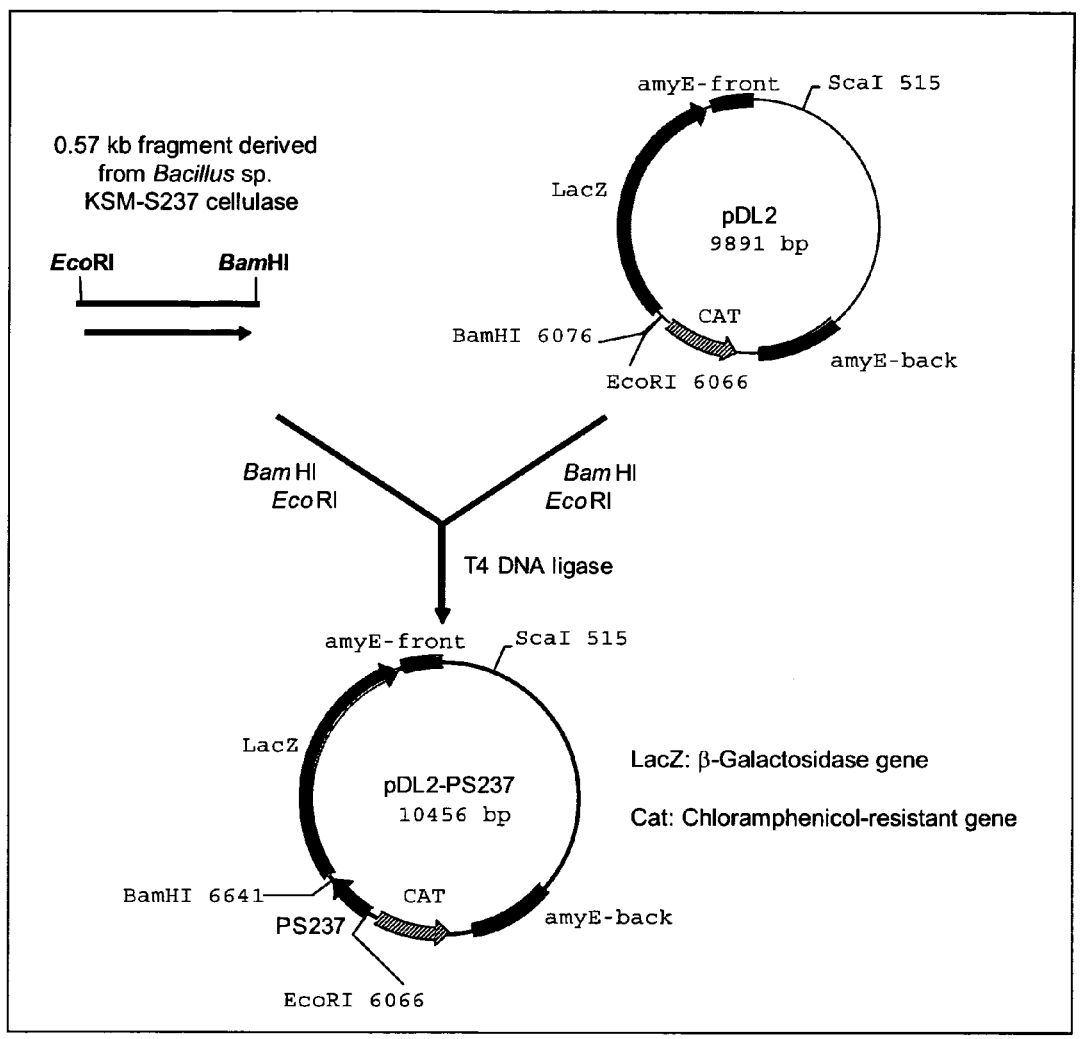
FIG. 2 A procedure for preparing a pDL2-S237 plasmid.
Figure 3:
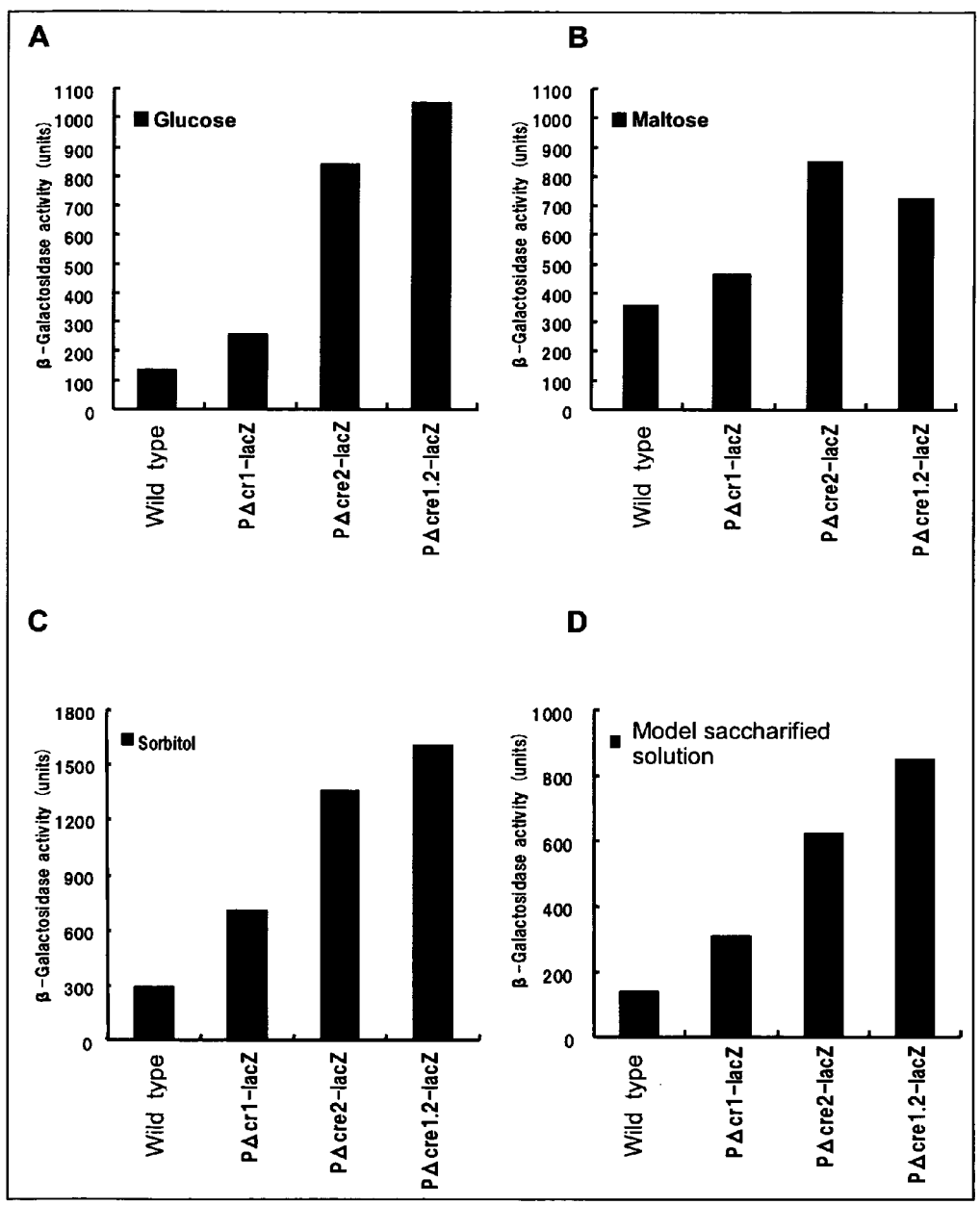
FIG. 3 β-galactosidase activity of the transformant of the present invention and that of a wild type. A: Activity in glucose-containing medium. B: Activity in maltose-containing medium. C: Activity in sorbitol-containing medium. D: Activity in model saccharified solution-containing medium.

Each of the promoter sequence DNA fragments prepared in Example 1 was cleaved by restriction enzymes EcoRI and BamHI and ligated to pDL2 plasmid (Fukuchi et al., Microbiology, 146, 1573-1583, 2000) cleaved out by EcoRI and BamHI. Cells of E. coli were transformed by use of the thus-obtained plasmid through a routine method, and the plasmid was recovered from the obtained transformant cells (see FIG. 2). Sequencing of the promoter sequence inserted into the obtained plasmid was performed by means of a 3100DNA sequencer (Applied Biosystems). A plasmid containing each promoter sequence DNA fragment prepared in Example 1 was recovered as an expression vector.

Example 3

Production of Transformants

The expression vector prepared in Example 2 was cleaved by a restriction enzyme ScaI to form fragments, and incorporated into cells of Bacillus subtilis 168 strain through the competent method for transformation. The thus-obtained cells were cultured in an LB agar medium containing ampicillin (1 µg/mL). From the grown colonies, a transformant in which the promoter region and a LacZ gene were incorporated into an amyE gene were recovered.

Example 4

Determination of β-Galactosidase Activity

Each transformant obtained in Example 3 was cultured in media containing a variety of carbon sources. The transcription efficiency of each promoter was evaluated by β-galactosidase activity as an index. As a carbon source, there was used a glucose, a maltose, sorbitol, or a model saccharified solution (carbohydrate solution imitating a biomass-derived carbon source: 4% glucose, 0.5% xylose, and 0.5% cellobiose). Each transformant was cultured in an LB medium (1 mL) at 30° C. for 12 hours, and the thus-obtained culture solution was inoculated to an LB medium (1 mL) containing a carbon source at a final concentration of 0.5% in such an amount that the final cell concentration was adjusted to 1%. The cells were cultured at 37° C. for 8 hours, and OD(600) was measured. A culture solution having a OD(600) of 1.0 was centrifuged to recover the cells. The cells were re-suspended in 25 mM Tris-HCl (pH: 7.4) (0.5 mL) to completely remove the culture medium, and the cells were re-collected through centrifugation. The thus-collected cells were suspended in Z buffer (60 mM $Na_2HPO_4$, 40 mM $NaH_2PO_4$, 10 mM KCl, 1 mM $MgSO_4/7H_2O$, and 2 mM DTT) (0.64 mL), and 2.5-mg/mL solution (0.16 mL) of lysozyme in Z buffer was added to the suspension. The mixture was incubated at 37° C. for 5 minutes to remove cell walls, whereby protoplast cells were prepared. To the protoplast cells, 10% Triton-X100 (8 µL) was added, and the thus-obtained admixture was employed as a lyzed cell solution. A control lyzed cell solution was prepared through the similar procedure from a wild-type strain into which lacZ was incorporated.

The β-galactosidase activity of each of the obtained lyzed cell solutions was determined through the ONPG method. Specifically, the lyzed cell solution was preliminarily incubated at 30° C. for three minutes, and a 4-mg/mL solution (0.2 mL) of ONPG in Z buffer was added thereto. From start of addition of the ONPG solution (0 sec), when the solution was yellowed by β-galactosidase activity, the reaction was terminated by adding 1M $Na_2CO_3$ (0.4 mL) to the solution. Insoluble fractions were removed through centrifugation, and OD(420) of each reaction mixture was measured, and β-galactosidase activity was calculated by the following equation:

$$\beta\text{-Galactosidase activity (Unit)} = 1000 \times OD(420)/\text{reaction time (min)}.$$

The results are shown in Table 2 and FIGS. 3A to 3D. In the case of culturing in a medium containing glucose, a transformant containing a Δcre1 promoter exhibited a β-galactosidase activity about 1.9 times that of the wild-type cell, and a transformant containing a Δcre2 promoter exhibited a β-galactosidase activity about 6.2 times that of the wild-type cell. A transformant containing a Δcre1.2 promoter (in which both Δcre1 and Δcre2 were deleted) exhibited a β-galactosidase activity about 7.8 times that of the wild-type cell, which is the highest transcription efficiency.

In the same experiment performed by use of maltose or sorbitol as a carbon source, the transcription efficiency of each promoter in the corresponding transformant was remarkably enhanced, as compared with the wild-type cell. In the experiment using the culture medium containing a carbon source imitating a carbohydrate solution of a biomass such as a plant (model saccharified solution), a remarkably enhanced transcription efficiency was also observed.

TABLE 2

| Carbon source | Strain | Transducing vector | β-Galactosidase activity (Unit) |
|---|---|---|---|
| Glucose | Wild type | PS237-lacZ | 135.2 |
| | Δcre1 | PΔcre1-lacZ | 256.8 |
| | Δcre2 | PΔcre2-lacZ | 840.5 |
| | Δcre1.2 | PΔcre1.2-lacZ | 1050.0 |
| Maltose | Wild type | PS237-lacZ | 354.0 |
| | Δcre1 | PΔcre1-lacZ | 462.9 |
| | Δcre2 | PΔcre2-lacZ | 850.0 |
| | Δcre1.2 | PΔcre1.2-lacZ | 723.8 |
| Sorbitol | Wild type | PS237-lacZ | 140.0 |
| | Δcre1 | PΔcre1-lacZ | 308.7 |
| | Δcre2 | PΔcre2-lacZ | 624.3 |
| | Δcre1.2 | PΔcre1.2-lacZ | 846.8 |
| Model saccharified solution | Wild type | PS237-lacZ | 290.7 |
| | Δcre1 | PΔcre1-lacZ | 706.4 |
| | Δcre2 | PΔcre2-lacZ | 1359.0 |
| | Δcre1.2 | PΔcre1.2-lacZ | 1604.8 |

What is claimed is:

1. A modified promoter, comprising a nucleotide sequence of a promoter derived from a bacterium belonging to the genus *Bacillus* in which at least one nucleotide sequence selected from the group consisting of a nucleotide sequence represented by SEQ ID NO: 1 and a nucleotide sequence represented by SEQ ID NO: 2 has been deleted, wherein the promoter derived from a bacterium belonging to the genus *Bacillus* is: a promoter of an alkaline cellulase gene from *Bacillus* sp. KSM-64 strain (FERM BP-2886); a promoter of an alkaline cellulase gene from *Bacillus* sp. KSM-S237 strain (FERM BP-7875); or a promoter containing a nucleotide sequence that has a sequence identity of 90% or more with respect to the nucleotide sequence of any one of said promoters and that has a nucleotide sequence represented by SEQ ID NO:1 or 2, or nucleotide sequences represented by SEQ ID NOs: 1 and 2.

2. A method for producing a modified promoter, the method comprising deleting, from a promoter derived from a bacterium belonging to the genus *Bacillus*, at least one nucleotide sequence selected from the group consisting of a nucleotide sequence represented by SEQ ID NO: 1 and a nucleotide sequence represented by SEQ ID NO: 2, wherein the promoter derived from a bacterium belonging to the genus *Bacillus* is: a promoter of an alkaline cellulase gene from *Bacillus* sp. KSM-64 strain (FERN BP-2886); a promoter of an alkaline cellulase gene from *Bacillus* sp. KSM-S237 strain (FERN BP-7875); or a promoter containing a nucleotide sequence that has a sequence identity of 90% or more with respect to the nucleotide sequence of any one of said promoters and that has a nucleotide sequence represented by SEQ ID NO:1 or 2, or nucleotide sequences represented by SEQ ID NOs: 1 and 2.

3. An expression vector comprising a modified promoter according to claim 1.

4. The expression vector according to claim 3, wherein the modified promoter is operably linked to the upstream of a gene encoding a gene product of interest.

5. A transformant comprising a modified promoter according to claim 1, wherein the modified promoter is operably linked to the upstream of a gene encoding a gene product of interest.

6. A method for producing a gene product of interest, wherein the method comprises employing a transformant according to claim 5 to produce said gene product of interest.

7. An expression vector comprising a modified promoter produced by the method according to claim 2.

8. The expression vector according to claim 7, wherein the modified promoter is operably linked to the upstream of a gene encoding a gene product of interest.

9. A transformant comprising a modified promoter produced by the method according to claim 2, wherein the modified promoter is operably linked to the upstream of a gene encoding a gene product of interest.

10. A method for producing a gene product of interest, wherein the method comprises employing the transformant according to claim 9 to produce said gene product of interest.

* * * * *